United States Patent
Lin et al.

(10) Patent No.: US 12,178,817 B2
(45) Date of Patent: Dec. 31, 2024

(54) COMPOUNDS FOR ENHANCING PPARγ EXPRESSION AND NUCLEAR TRANSLOCATION AND THERAPEUTIC USE THEREOF

(71) Applicant: REALINN LIFE SCIENCE LIMITED, Taoyuan (TW)

(72) Inventors: Jen Cheng Lin, Keelung (TW); Chun-Chieh Lin, Taipei (TW); Hsu-Tung Lee, Taichuang (TW); Yu-Ming Fan, Taipei (TW); Jui-Chi Tsai, Taipei (TW); Ying-Chi Du, Chiayi (TW)

(73) Assignee: REALINN LIFE SCIENCE LIMITED, Taoyuan (TW)

( * ) Notice: Subject to any disclaimer, the term of this patent is extended or adjusted under 35 U.S.C. 154(b) by 0 days.

(21) Appl. No.: 15/546,949

(22) PCT Filed: Jan. 27, 2016

(86) PCT No.: PCT/CN2016/072347
§ 371 (c)(1),
(2) Date: Jul. 27, 2017

(87) PCT Pub. No.: WO2016/119701
PCT Pub. Date: Aug. 4, 2016

(65) Prior Publication Data
US 2018/0015090 A1    Jan. 18, 2018

Related U.S. Application Data

(60) Provisional application No. 62/108,564, filed on Jan. 28, 2015.

(51) Int. Cl.
*A61K 31/519*    (2006.01)
*A61K 9/127*    (2006.01)

(52) U.S. Cl.
CPC ............ *A61K 31/519* (2013.01); *A61K 9/127* (2013.01); *A61K 9/1271* (2013.01)

(58) Field of Classification Search
CPC .................................................. A61K 31/519
See application file for complete search history.

(56) References Cited

U.S. PATENT DOCUMENTS

| 3,031,450 A |   | 4/1962 | Fischer et al. |
| 6,037,346 A | * | 3/2000 | Doherty, Jr. ......... A61K 31/522 |
|             |   |        | 514/250 |

(Continued)

FOREIGN PATENT DOCUMENTS

| CN | 1382052 A | 11/2002 |
| CN | 1481244 A | 3/2004 |

(Continued)

OTHER PUBLICATIONS

Bucciarelli (The acute respiratory distress syndrome in catastrophic antiphospholipid syndrome, Ann. Rheum. Dis. 65, pp. 81-86, (Year: 2006)).*

(Continued)

*Primary Examiner* — Benjamin J Packard
(74) *Attorney, Agent, or Firm* — Sughrue Mion, PLLC

(57) ABSTRACT

The present invention relates to a novel type of PPARγ modulator having a pyrimido[5,4-d]pyrimidine main structure. The PPARγ modulator can enhance the expression and nuclear translocation of PPARγ in cells. The present invention also relates to a pharmaceutical composition comprising the PPARγ modulator of the invention encapsulated in a pharmaceutically acceptable cell-penetrating drug delivery system so that it can be directly delivered into cells. The present invention thus provides a method of preventing or treating PPARγ-related disorders or conditions comprising administering to a subject in need thereof a therapeutically (Continued)

effective amount of the PPARγ modulator of the invention or the pharmaceutical composition of the invention.

15 Claims, 17 Drawing Sheets

(56) References Cited

U.S. PATENT DOCUMENTS

| | | | |
|---|---|---|---|
| 8,106,061 | B2 | 1/2012 | Forssmann |
| 2002/0028219 | A1* | 3/2002 | Smyth-Templeton ...................... A61K 9/1272 424/400 |
| 2003/0181461 | A1 | 9/2003 | Lautt et al. |
| 2004/0063730 | A1 | 4/2004 | Eggenweiler et al. |
| 2005/0038003 | A1* | 2/2005 | Gilbert ...................... A61P 9/10 514/165 |
| 2007/0270723 | A1 | 11/2007 | Krebs et al. |
| 2008/0138400 | A1* | 6/2008 | Kurzrock ............. A61K 9/1272 514/679 |
| 2013/0251814 | A1 | 9/2013 | Hua et al. |

FOREIGN PATENT DOCUMENTS

| | | | |
|---|---|---|---|
| CN | 1969939 A * | 5/2007 | |
| CN | 101780037 A | 7/2010 | |
| CN | 104971043 A | 10/2015 | |
| EP | 0344643 A2 | 12/1989 | |
| EP | 0457671 A2 | 11/1991 | |
| EP | 1093814 A1 | 4/2001 | |
| JP | 2003-506394 A | 2/2003 | |
| JP | 2003-516363 A | 5/2003 | |
| JP | 2003518066 A | 6/2003 | |
| JP | 2004525979 A | 8/2004 | |
| JP | 2006-517557 A | 7/2006 | |
| JP | 2011-506607 A | 3/2011 | |
| KR | 1020100111839 A | 10/2010 | |
| WO | 9423723 A1 | 10/1994 | |
| WO | 01/10406 A2 | 2/2001 | |
| WO | 01/30353 A1 | 5/2001 | |
| WO | 01/41807 A2 | 6/2001 | |
| WO | 0145713 A1 | 6/2001 | |
| WO | 02085368 A2 | 10/2002 | |
| WO | 03/030823 A2 | 4/2003 | |
| WO | 03/061638 A2 | 7/2003 | |
| WO | 2004/071385 A2 | 8/2004 | |
| WO | 2004069254 A2 | 8/2004 | |
| WO | 2005/120474 A2 | 12/2005 | |
| WO | 2008101469 A2 | 8/2008 | |
| WO | 2009/078998 A1 | 6/2009 | |
| WO | 2010034837 A1 | 4/2010 | |
| WO | 2011038298 A1 | 3/2011 | |
| WO | 2014/121211 A2 | 8/2014 | |
| WO | 2014141079 A1 | 9/2014 | |

OTHER PUBLICATIONS

Tzanakakis (Prevention of Human Pancreatic Cancer Cell I Hepatic Metastasis in Nude Mice by Dipyridamole and Its Analog RA-233, Cancer, Apr. 15, 71(8) pp. 2466-2471 (Year: 1993).*

Cheng et al (International Journal of Pharmaceutics 313 (2006) 136-143). (Year: 2006).*

Berasain et al ((2009), Inflammation and Liver Cancer. Annals of the New York Academy of Sciences, 1155: 206-221). (Year: 2009).*

Akchurin et al (Blood Purif (2015) 39 (1-3): 84-92). (Year: 2015).*

Office Action and Search Report dated Sep. 26, 2017, issued by the Taiwan Patent Office in corresponding Taiwanese Application No. 105102559.

Cheng Ji, et al., "Preparation of amylopectin modified dipyridamole liposome and its tissue distribution in mice", Acta Pharmaceutica Sinica 2006 41(3): 277-281.

Cheng Ji et al, "Characterization, lung targeting profile and therapeutic efficiency of dipyridamole liposomes", Journal of Drug Targeting, Dec. 2006, 14(10):717-723.

Chien-Chung Wang, "Study on the effect of persantin (dipyridamole) in lipopolysaccharide-inducing liver injury in rats", Chung Shan Medical University, Institute of Biochemistry and Biotechnology, Master Thesis, 2009 (published on Mar. 11, 2010), 2 pages total.

Communication, dated Jun. 28, 2018, issued by the European Patent Office in European Patent Application No. 16742763.2.

Communication dated Aug. 14, 2019 from the State Intellectual Property Office of the P.R.C. in application No. 201680003479.1.

Communication dated Aug. 22, 2019 from the European Patent Office in application No. 16742763.2.

Notice of Reasons for Rejection dated Oct. 8, 2019 from the Japanese Patent Office in application No. 2017-540787.

Drug Package Insert, "Dipyridamole Intravenous Injection Solution 10mg", Jun. 2014, total 4 pages.

Drug Package Insert, "Dipyridamole Tablet 25mg", Jun. 2013, total 4 pages.

Communication dated, Jun. 9, 2020, issued by the Japanese Patent Office in JP Application No. 2017-540787.

Communication, dated Jul. 31, 2020, issued by the State Intellectual Property Office of the P.R.C. in Application No. 201680003479.1.

Communication, dated Sep. 7, 2020, issued by European Patent Office in counterpart application No. 16 742 763.2.

Office Action, dated May 25, 2022, issued by the Canadian Patent Office in Canadian Application No. 2,975,000.

Guo, Ruxuan et al., "Glomerular Disease and Its Progress", Henan Medical University Press, Oct. 1995 1st edition, p. 76, published on Oct. 31, 1995 (6 pages total).

Jiang, Jijie, "Modern Nephrology" published by People's Military Medical Publishing House, Aug. 2001, 1st Edition, pp. 371-372 (8 pages total).

Sun, Chuanxing, "Clinical Disease Diagnosis Based on Cure and Improvement Criteria", The People's Republic of China, Compiled by the Ministry of Health of the General Logistics Department of the People's Liberation Army, People's Military Medical Press, Jun. 1998, 2nd edition, p. 83, published on Jun. 30, 1998 (6 pages total).

Bao, Long-distance and Zhao, Hanzhang "Criteria for Diagnosis and Efficacy of Children's Diseases", Jilin Science and Technology Press, Sep. 1993 1st edition, p. 220, published on Sep. 30, 2009 (5 pages total).

Luo, Mingsheng et al., "Compendium of Pharmaceutical Excipients", Sichuan Science and Technology Press, 2nd Edition, Jan. 2006, p. 703, published on Jan. 31, 2006 (5 pages total).

Qiu, Xueyou, "Pharmacist's Handbook", People's Military Medical Publishing House, Jul. 1998 2nd Edition, p. 575, published on Jul. 31, 1998 (8 pages total).

Liu, Gengtao, "Contemporary Pharmacology", China Union Medical College Press, May 2008 Second Edition, p. 715 , published on May 31, 2008 (4 pages total).

Zhou, Beilun et al., "Latest Advances in Autoimmune Hepatitis", "Internal Medicine", vol. 20, pp. 209-219, 2009 (12 pages total).

Shen, Zhenrong et al., "New progress of partial segmental glomerulosclerosis", Internal Medicine, 1999, vol. 10, pp. 177-184. (15 pages total).

Office Action dated May 5, 2022 from the China National Intellectual Property Administration in CN Application No. 201680003479. 1.

European Office Action issued on Jul. 25, 2023 from the European Patent Office in corresponding European Application No. 16 742 763.2.

Hung et al., "Dipyridamole treatment is associated with improved renal outcome and patient survival in advanced chronic kidney disease", Kaohsiung Journal of Medical Science (2014) 30, 599-607.

Written Opinion for PCT/CN2016/072347, dated May 9, 2016, issued by the International Bureau.

International Search Report for PCT/CN2016/072347, dated May 9, 2016, issued by the International Bureau.

* cited by examiner

COMPOUNDS FOR ENHANCING PPARγ EXPRESSION AND NUCLEAR TRANSLOCATION AND THERAPEUTIC USE THEREOF

FIELD OF THE INVENTION

The invention provides a method of enhancing the expression and nuclear translocation of PPARγ and related therapeutic use.

BACKGROUND OF THE INVENTION

Among the nuclear receptor families, peroxisome proliferator activated receptors (PPARs) have been attracting attentions over the past decade. PPARs are nuclear transcription factors activated by their ligand and act as crucial regulatory factors in the metabolic syndrome (Guan, Y. J. Am. Soc. Nephrol, 2004, 15, 2801-2815). Therefore, PPARs play an important role in the genesis, development and control of diseases such as insulin resistance, impaired glucose tolerance, Type II diabetes, obesity, hyperlipidemia, hypertension, angiocardiopathy, artherosclerosis, etc.

PPARs are classified into three subtypes: PPARα, PPARδ and PPARγ, which regulate expression of the gene by binding to a specific DNA sequence of a gene (Berger, J. et al., The Journal of Biological Chemistry, 1999, 274 (10), 6718-6725). PPARα is mainly expressed in the liver, heart, intestinal tract, kidney and macrophage, and, after being activated, can increase the metabolism of fatty acids, alleviate inflammatory response in macrophages, and reduce low density lipoprotein cholesterol; PPARγ is expressed in the adipocyte, placentoma and other tissues, and, after being activated, can not only lower blood glucose level and increase insulin sensitivity, but also plays a key role in lipid metabolism, cytokine antagonization, anti-inflammation, immune-regulation, blood pressure regulation, etc. (Kasuga, J. et al., Bioorg. Med. Chem. 2007, 15, 5177-5190; U.S. Pat. No. 8,822,519 B2).

PPARγ containing three isoforms, γ1, γ2 and γ3, are transcribed from the same gene through alternative splicing and display different tissue specificity. PPARγ 1 and γ3 are identical in length; however, γ2 contains an additional N-terminal region of 28 amino acids. All PPARγ isoforms can be activated by the anti-diabetic agents thiazolidinediones (TZDs). TZDs act by targeting PPARγs in nucleus and thus improve insulin resistance, majorly in adipose tissue, and act in liver and skeletal muscle in a minor way where PPARγ has lower expression. PPARγ is essential for adipocyte differentiation because PPARγ could modulate expression of genes in adipose tissue. Ligand-induced activation causes enhancement in lipid metabolism, lipid uptake and insulin action, and attenuation in lipolysis and free fatty acid (FFA) release. Therefore, circulating FFAs are decreased and lipid levels in adipose tissue are increased. It has been proposed that PPARγ agonist improves hyperglycemia, which responds to highly FFA-induced insulin resistance by redistributing the lipids away from liver and muscle. Fatty acids that drain from visceral adipose tissue into subcutaneous fat causes reduction in glucose production of liver and improvement of glucose homeostasis. PPARγ ligand is also associated with regulation of adipokine synthesis in adipose tissue, such as tumor necrosis factor-α (TNF-α), interleukin-6 (IL-6), resistin, leptin, adiponectin, that affects insulin action. TNF-α, IL-6, and resistin could lead to insulin resistance, whereas leptin and adiponectin may improve insulin sensitivity. In addition, PPARγ reduces the expression and thus accumulation of pro-inflammatory cytokines, such as TNF-α, and chemokines of macrophage in the adipose tissue of obese and insulin-resistant rodents in which insulin signal transduction is inhibited. Thus, PPARγ agonists contribute to anti-inflammation. Consequently, PPARγ activation would lead to insulin sensitivity improvement in liver and skeletal muscle, and hyperglycemia mitigation (Peng, Yi-Hui, Structure based drug design of peroxisome proliferator-activated receptor (PPAR) agonists, Doctoral Dissertation, National Tsing Hua University, 2010).

Many diseases are associated with the regulation of PPARγ. PPARγ agonists have been used in the treatment of diabetes mellitus and other diseases that feature insulin resistance. However, in addition to diabetes mellitus, researchers found that PPARγ involves multiple regulatory mechanisms and is a potential target for the treatment of various diseases including: atherosclerosis, dyslipidemia, obesity and syndrome X, cardiovascular diseases, inflammation and neurology diseases, Alzheimer's disease, multiple sclerosis, Parkinson's disease, ischemic stroke, spinal cord injury, psoriatic arthritis, and chronic obstructive pulmonary disease. PPARγ is also reported to be associated with eye diseases, viral infections, renal diseases, polycystic ovarian diseases, inflammatory bowel diseases, asthma, diseases of the bone, aging and longevity, drug metabolism, wound healing, acne, and mitochondrial dysfunction diseases (Kumar A, Hasamnis A. A clinical update on peroxisome proliferator-activated receptors. Syst Rev Pharm 2010; 1:175-81).

It is reported that PPARs have an inflammation regulatory effect. Particularly, it can regulate inflammatory response after tissue injury. According to the research on stroke, ischemia/reperfusion (I/R) injury represents a challenging pathophysiological condition with serious clinical implications, in a broad range of conditions such as organ transplantation, compartment syndrome, myocardial infarction, stroke, and hemorrhagic, traumatic, or septic shock. Tissue ischemia together with subsequent reperfusion has been shown to trigger a whole cascade of inflammatory events that, if not counteracted in the early stages, result in cell necrosis with irreversible tissue damage in affected organs. Research efforts in recent years have provided increasing evidence that PPARs represent major regulators of this inflammatory response; PPAR activation could be shown to restrict inflammation and exert multiple beneficial effects against ischemia/reperfusion injury. Consequently, pharmacological agents targeting PPARs have been suggested as potential therapeutics for the treatment of I/R (Neher M D, Weckbach S, Huber-Lang M S, Stahel P F. New insights into the role of peroxisome proliferator-activated receptors in regulating the inflammatory response after tissue injury. PPAR Res. 2012; 2012:728461).

Similarly to its role in traumatic central nervous system (CNS) injuries, a strong relationship between PPAR tissue expression and I/R injury can be demonstrated. In kidney I/R, PPARγ expression is strongly increased in endothelial cells, interstitial cells, and collecting ducts of the kidney peaking from 1.5 to 5 hours after reperfusion. Similar up-regulation of PPARγ was detected in the cortical peri-infarct area after focal cerebral ischemia in rats. Interestingly, Lee and colleagues (C. H. Lee, O. K. Park, K. Y. Yoo et al., "The role of peroxisome proliferator-activated receptor γ, and effects of its agonist, rosiglitazone, on transient cerebral ischemic damage," Journal of the Neurological Sciences, vol. 300, no. 1-2, pp. 120-129, 2011) have recently found in a model of transient cerebral ischemia that PPARγ- immunoreactivity in the hippocampus was colocalized with microglial cells indicating a high functional state of microglia in the ischemic brain.

In recent years, animal studies of I/R injury in various organs have revealed a crucial role of PPARs in reducing or even preventing tissue injury and organ dysfunction after ischemia and reperfusion. Consequently, a wide variety of natural and synthetic PPAR agonists have been tested in experimental I/R models and been shown to significantly improve the outcome of I/R injury. The mechanisms of tissue protection by PPAR ligands have been thought to be multifactorial, since these agonists can interact with variable parameters of the IR-induced inflammatory cascade and inhibit multiple targets on the way to injury progression. The proposed mechanisms of action include: (i) reduced expression of adhesion molecules like ICAM-1 and p-selectin on endothelial cells, (ii) decreased vascular permeability with suppressed edema formation, (iii) inhibited release of pro-inflammatory mediators like cytokines and chemokines, (iv) reduced activation of inflammatory cells like neutrophils, (v) decreased formation of reactive oxygen species, (vi) suppressed cell apoptosis and necrosis, and (vii) inhibited platelet aggregation and thrombus formation. Similarly to CNS injuries, the majority of these anti-inflammatory effects are initiated by PPAR-induced suppression of transcription factors (mainly NF-κB) and subsequent inhibition of pro-inflammatory gene transcription. In addition to the mentioned general effects of PPAR activation on the inflammatory response in I/R, numerous tissue-specific impacts of PPAR agonists in different organ systems have been described.

Renal ischemia is a major cause of acute renal failure that is complicated by the fact that subsequent reperfusion of hypoxic tissue may cause additional injury. Agonists to all three PPAR isoforms, PPARα, PPARβ/δ, and PPARγ, significantly reduce tissue damage in mice subjected to kidney ischemia and reperfusion. This reno-protection is reflected in attenuation of cortical and medullary necrosis, reduction of histological signs of renal damage, and finally in strongly increased renal function with lowered serum creatinine and urea nitrogen levels. The mechanisms underlying these beneficial properties may consist of induction of fatty acid β-oxidation enzymes by PPARs in kidney tissue; transgenic mice expressing PPARα in the proximal tubule have been shown to exert increased fatty acid oxidation and be protected from I/R-induced kidney failure.

I/R injury of the lung still occurs in 20% of patients after lung transplantation and remains the main cause of death during the first month after transplantation (R. C. King, O. A. R. Binns, F. Rodriguez et al., "Reperfusion injury significantly impacts clinical outcome after pulmonary transplantation," Annals of Thoracic Surgery, vol. 69, no. 6, pp. 1681-1685, 2000). Application of the synthetic PPARγ ligand pioglitazone or the natural PPARγ agonist 15-deoxy-Δ12, 14-prostaglandin J2 (15d-PGJ2) before ischemia could attenuate lung I/R injury in rats. A recent study by Okada et al. (M. Okada, S. F. Yan, and D. J. Pinsky, "Peroxisome proliferator-activated receptor-γ (PPAR-γ) activation suppresses ischemic induction of Egr-1 and its inflammatory gene targets," FASEB Journal, vol. 16, no. 14, pp. 1861-1868, 2002) indicated that PPARγ activation suppresses activation of the zinc finger transcription factor early growth response gene-1 (Egr-1), which has a crucial role in the inflammatory response in ischemic vessels. Thus, as a consequence of PPARγ activation, the induction of Egr-1 target genes such as interleukin-1β is prevented, IR-associated leukostasis is decreased, and overall survival is improved.

Intestinal and gastric I/R injuries are serious clinical conditions resulting from abdominal aneurism, acute mesenteric ischemia, small bowel transplantation, or shock. In rodent models of intestinal I/R, all three isotypes of PPAR agonists showed profound anti-inflammatory, anti-oxidative and anti-apoptotic effects that were associated with a decreased I/R-induced mortality rate. Similarly, pioglitazone and rosiglitazone suppressed gastric-mucosal erosion and damage in gastric I/R rats. Additionally, beneficial effects of early enteral nutrition after gut I/R could be linked to PPAR induction. The nutrition component glutamine has been reported to exert gut protection by activation of PPARγ.

Ischemic cerebrovascular disease represents the third leading cause of death and is one of the major causes of neurological dysfunction and disability. Various studies have suggested that PPAR agonists may prevent or decrease the severity of both focal and global ischemia. In humans, stroke incidence was reduced when men with coronary heart disease and low HDL and LDL cholesterol values were treated with the fibrate and PPARα agonist gemfibrozil. Application of PPARα, PPARβ/δ, and PPARγ ligands in transient ischemic brain injury of rodents resulted in significantly attenuated neuronal damage and reduced infarction volume, increased cerebral blood flow, and improved neurological outcome parameters. This neuroprotection was observed when animals were treated preventively before ischemia, at the time of cerebral infarction, or shortly after with a time window of efficacy of two hours after ischemia. In contrast to transient ischemia, PPARγ activation failed to decrease infarction volume when blood flow was interrupted permanently without subsequent reperfusion. These findings support evidence that the neuroprotective role of PPARγ is specific to events occurring during reperfusion.

Overall, various studies provide evidence that ligands to PPARs cause a substantial reduction of I/R injury in diverse organs by interfering with multiple targets of the I/R-induced inflammatory cascade.

PPARγ-based PPAR agonists have the properties of anti-inflammation, anti-oxidation and anti-MMPs and can provide protection to cells. Hence, in addition to acute ischemic diseases, such PPARγ agonists are particularly suitable for the treatment of acute organ injuries, including acute lung injury, acute renal injury, acute liver injury, acute myocarditis, acute myocardial infarction, acute gastro-intestinal injury and acute peritonitis. In addition, due to the capability of treating multiple organ injuries, PPARγ agonists can treat diseases such as sepsis and cardiorenal syndrome that clinically cause multiple organ injuries. By modification of their dosage form and carriers to prolong the half-life and control release properties of the drugs, PPARγ agonists can be used in the treatment of chronic inflammatory diseases.

Clinically available PPARγ agonists include agents for reducing blood glucose, such as TZDs and agents for lowering blood lipids, such as statins.

TZDs are effective oral hypoglycemic agents (see FIG. 1). The pharmacological action has been proven to be activating PPARγ. However, TZDs have many side effects. For example, troglitazone causes hepatitis and has been taken off the shelf since 2000; France and Germany have suspended the use of pioglitazone because reports indicate that this drug may increase the risk of bladder cancer; and use of rosiglitazone has been suspended in the United Kingdom and the European Union since 2010 due to increased risk of cardiovascular diseases.

PPARγ agonists currently under experimentation include netoglitazone and rivoglitazone. Early developed but not yet approved drugs include ciglitazone. These drugs still have the main chemical skeleton of thiazolidinedione, and thus may still increase the risk of liver inflammation, bladder cancer and cardiovascular diseases.

Statins are pharmaceutical agents for lowering blood lipid levels (see FIG. 2). The pharmacological action of statins is mainly the inhibition of HMG-CoA. Statins are characterized in the chemically modified structure based on the main backbone of the target enzyme substrate HMG-CoA. Statins include lovastatin, pravastatin, simvastatin, fluvastatin, rosuvastatin, atorvastatin, and pitavastatin. It is reported that statins can activate PPAR.

Other PPAR dual (alpha and gamma) agonistic drugs include tesaglitazar, ragaglitazar, naveglitazar and muraglitazar (see FIG. 3). They are used for treating type 2 diabetes mellitus and dyslipidemia. However, there are toxicity concerns for these drugs identified by the US FDA.

In view of the above, currently available drugs that modulate PPAR activity or expression are mainly those having thiazolidinedione main backbone or HMG-CoA analogues. The choice of clinically safe and effective PPARγ agonists is limited. Currently available PPARγ agonists still incur potential risk of side effects. There is a need to provide novel PPARγ modulators that can be used in the treatment of PPARγ-related disorders or conditions.

U.S. Pat. No. 3,031,450 discloses substituted pyrimido[5,4-d]pyrimidine compounds having the following formula:

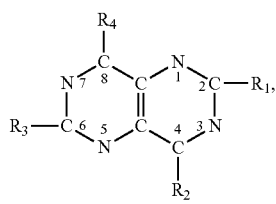

wherein two, three or all four of the substitutents $R_1$ through $R_4$ are basic moieties selected from the group consisting of amino, lower alkylamino, dialkylamino wherein the alkyl moieties have from 1 to 12 carbon atoms, mono-(hydroxy-lower alkyl)amino, di-(hydroxy-lower alkyl)-amino, (hydroxy-lower alkyl)-alkylamino wherein the alkyl moiety has from 1 to 12 carbon atoms, (lower alkoxy-lower alkyl)-amino, lower alkenyl-amino, cyclohexyl-amino, halophenyl-amino, nitrophenyl-amino, (lower alkoxy-phenyl) amino, [(di-lower alkyl-amino)-phenyl]-amino, benzylamino, semicarbazidyl, hydrazinyl, guanidyl, ethyleneimino, piperidyl, lower alkyl-piperidyl, lower alkoxy-piperidyl, hydroxy-piperidyl, pyrrolidyl, lower alkyl-pyrrolidyl, lower alkoxy-pyrrolidyl, hydroxy-pyrrolidyl, morpholyl, lower alkyl-morpholyl, lower alkoxy-morpholyl, hydroxy-morpholyl, tetrahydropyridyl, lower alkyl-tetrahydropyridyl, lower alkoxy-tetrahydropyridyl, hydroxy tetrahydropyridyl, hexamethyleneimino, lower alkyl-hexamethyleneimino, lower alkoxy-hexamethyleneimino, hydroxy-hexamethyleneimino, tetrahydroquinolyl, lower alkyl-tetrahydroquinolyl, lower alkoxy-tetrahydroquinolyl, hydroxy-tetrahydroquinolyl, piperazyl, lower alkylpiperazyl, lower alkoxy-piperazyl, hydroxy-piperazyl and N'-lower alkylpiperazyl, and the remaining substituents $R_1$ to $R_4$ are selected from the group consisting of hydrogen, halogen, hydroxyl, mercapto, lower alkyl, phenyl, lower alkoxy, di-lower-alkyl-amino-lower alkoxy and lower alkyl-thio, phenyl-thio, benzyl-thio, lower alkoxy-lower alkoxy, their non-toxic alkali metal salts and their non-toxic acid addition salts. Among these compounds, dipuridamole is of particular interest.

Dipyridamole is a substituted pyrimido[5,4-d]pyrimidine compound having structural formula (I):

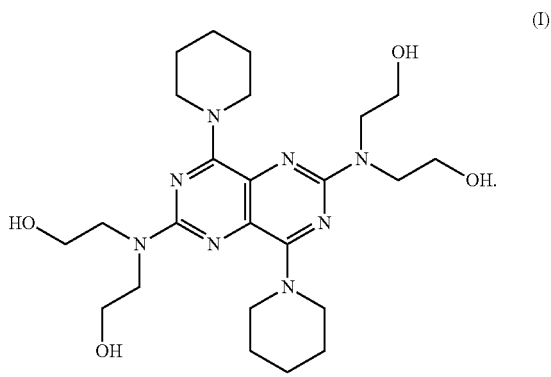 [SMILES: OCCN(CCO)c1nc(N2CCCCC2)c2nc(N(CCO)CCO)nc(N3CCCCC3)c2n1]

It is known that dipyridamole can inhibit phosphodiesterase (PDE) and the uptake of adenosine. However, animal studies reveal that a high dose is not therapeutically acceptable. Previous research found that high dose dipyridamole will cause accumulation of adenosine in renal tissues and consequently increase the side effects of vasoconstriction and reduction of renal blood flow, particularly in small mammals such as cats and dogs (Arend L J, Thompson C I, and Spielman W S. Dipyridamole decreases glomerular filtration in the sodium-depleted dog. Evidence for mediation by intrarenal adenosine. Circ Res 56: 242-251, 1985; Thompson C I, Sparks H V, and Spielman W S. Renal handling and production of plasma and urinary adenosine. Am J Physiol Renal Fluid Electrolyte Physiol 248: F545-F551, 1985; Arend L J, Bakris G L, Burnett J C Jr Megerian C, and Spielman W S. Role for intrarenal adenosine in the renal hemodynamic response to contrast media. J Lab Clin Med 110: 406-411, 1987; Katholi R E, Taylor G J, McCann W P, Woods W T Jr, Womack K A, McCoy C D, Katholi C R, Moses H W, Mishkel G J, and Lucore C L. Nephrotoxicity from contrast media: attenuation with theophylline. Radiology 195: 17-22, 1995). In addition, Lin et al. (Lin J J, Churchill P C, and Bidani A K. The effect of dipyridamole on the initiation phase of postischemic acute renal failure in rats. Can J Physiol Pharmacol 65: 1491-1495, 1987) discloses that administering dipyridamole will exacerbate the condition of mice suffering from postischemic acute renal failure. Hence, dipyridamole is considered unsuitable for use in small mammals. Intravenous injection of dipyridamole to induce vasodilation as used in cardiography in nuclear medicine serves as an example that administrating dipyridamole in a large amount during a short period will cause hypotension. Therefore, a method of reducing the therapeutic dose of dipyridamole in clinical treatment is needed.

SUMMARY OF THE INVENTION

It is found in the present invention that certain substituted pyrimido[5,4-d]pyrimidine compounds such as dipyridamole are capable of enhancing the expression and nuclear translocation of PPARγ. Therefore, the present invention provides a novel type of PPARγ modulators having the pyrimido[5,4-d]pyrimidine main structure and a method of preventing or treating PPARγ-related disorders or conditions, such as insulin resistance, impaired glucose tolerance, Type II diabetes, obesity, hyperlipidemia, hypertension, angiocardiopathy, atherosclerosis, dyslipidemia, obesity and syndrome X, cardiovascular diseases, inflammation and neurology diseases, Alzheimer's disease, multiple sclerosis, Parkinson's disease, ischemic stroke, spinal cord injury, psoriatic arthritis, chronic obstructive pulmonary disease, eye diseases, viral infections, polycystic ovarian disease, inflammatory bowel disease, asthma, diseases of the bone, aging and longevity, drug metabolism, wound healing, acne, mitochondrial dysfunction diseases, ischemic stroke, renal diseases, liver diseases, lung diseases, cardiovascular diseases, autoimmune disorders, and systemic inflammatory response syndrome (sepsis), using such PPARγ modulators. The invention also relates to a method of increasing the expression and nuclear translocation of PPARγ.

In an embodiment, the invention relates to a method of preventing or treating PPARγ-related disorders or conditions, comprising administering to a subject in need thereof a therapeutically effective amount of a PPARγ modulator, preferably a compound of formula I:

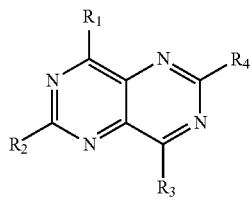

wherein each of $R_1$, $R_2$, $R_3$ and $R_4$ is independently selected from the group consisting of heterocyclyl and di(hydroxyalkyl)amino, or a pharmaceutically acceptable salt thereof.

In another embodiment, the present invention provides a method of preventing or treating PPARγ-related diseases, comprising administering to a subject in need thereof a pharmaceutical composition comprising a therapeutically effective amount of a compound of formula I or a pharmaceutically acceptable salt thereof encapsulated in a pharmaceutically acceptable cell-penetrating drug delivery system.

The present invention also relates to use of a compound of formula I or a pharmaceutically acceptable salt thereof in the manufacture of a medicament for preventing or treating PPARγ-related disorders or conditions. In a preferred embodiment, the medicament comprises a compound of formula I or a pharmaceutically acceptable salt thereof encapsulated in a pharmaceutically acceptable cell-penetrating drug delivery system.

The present invention further relates to a pharmaceutical composition for preventing or treating PPARγ-related diseases, comprising a therapeutically effective amount of a compound of formula I or a pharmaceutically acceptable salt thereof encapsulated in a pharmaceutically acceptable cell-penetrating drug delivery system. In a preferred embodiment, the compound is dipyridamole and the cell-penetrating drug delivery system is a liposome.

The present invention is described in detail in the following sections. Other characterizations, purposes and advantages of the present invention can be easily found in the detailed descriptions and claims of the invention.

DETAILED DESCRIPTION OF THE INVENTION

Figure 1:
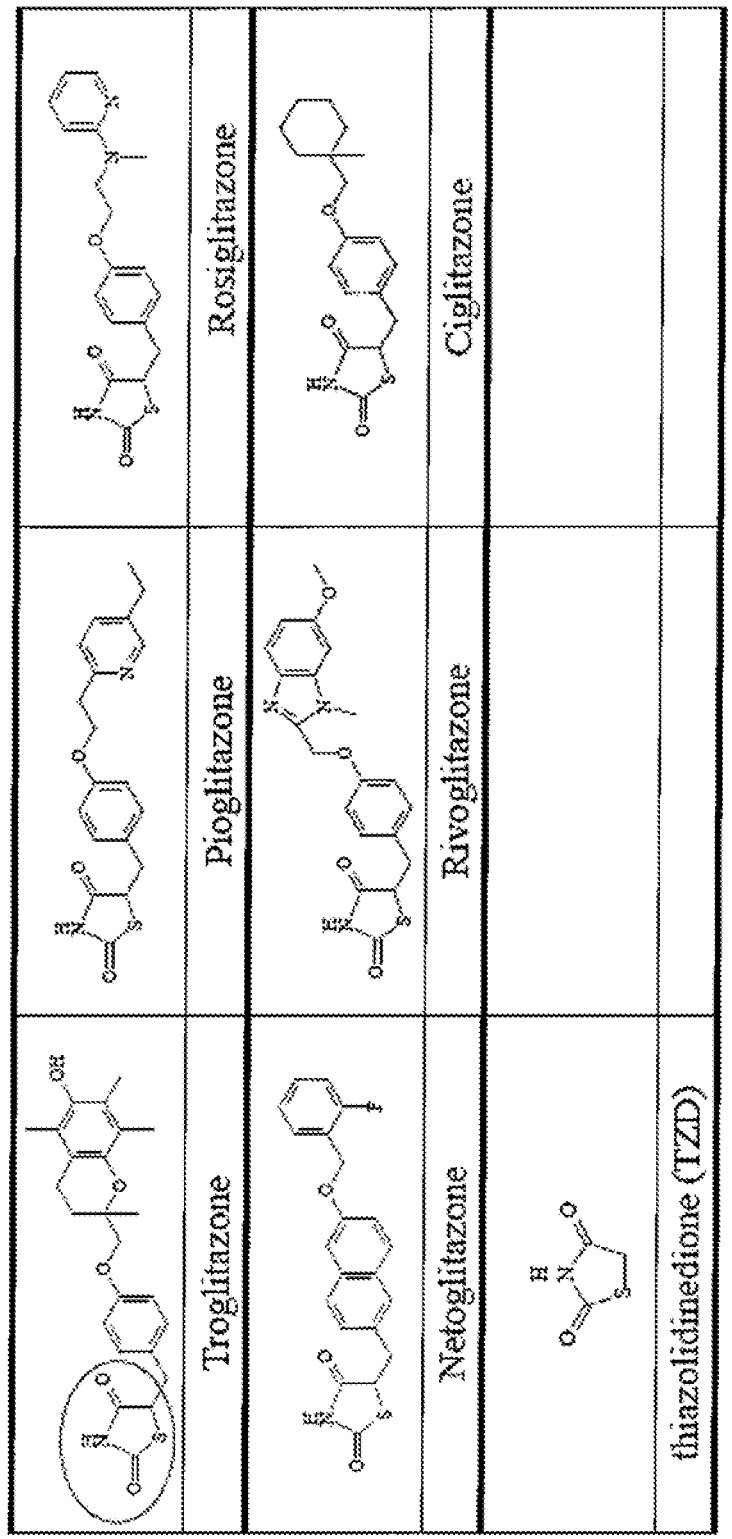
FIG. 1 shows the chemical structures of the thiazolidinedione (TZD) drugs.
Figure 2:
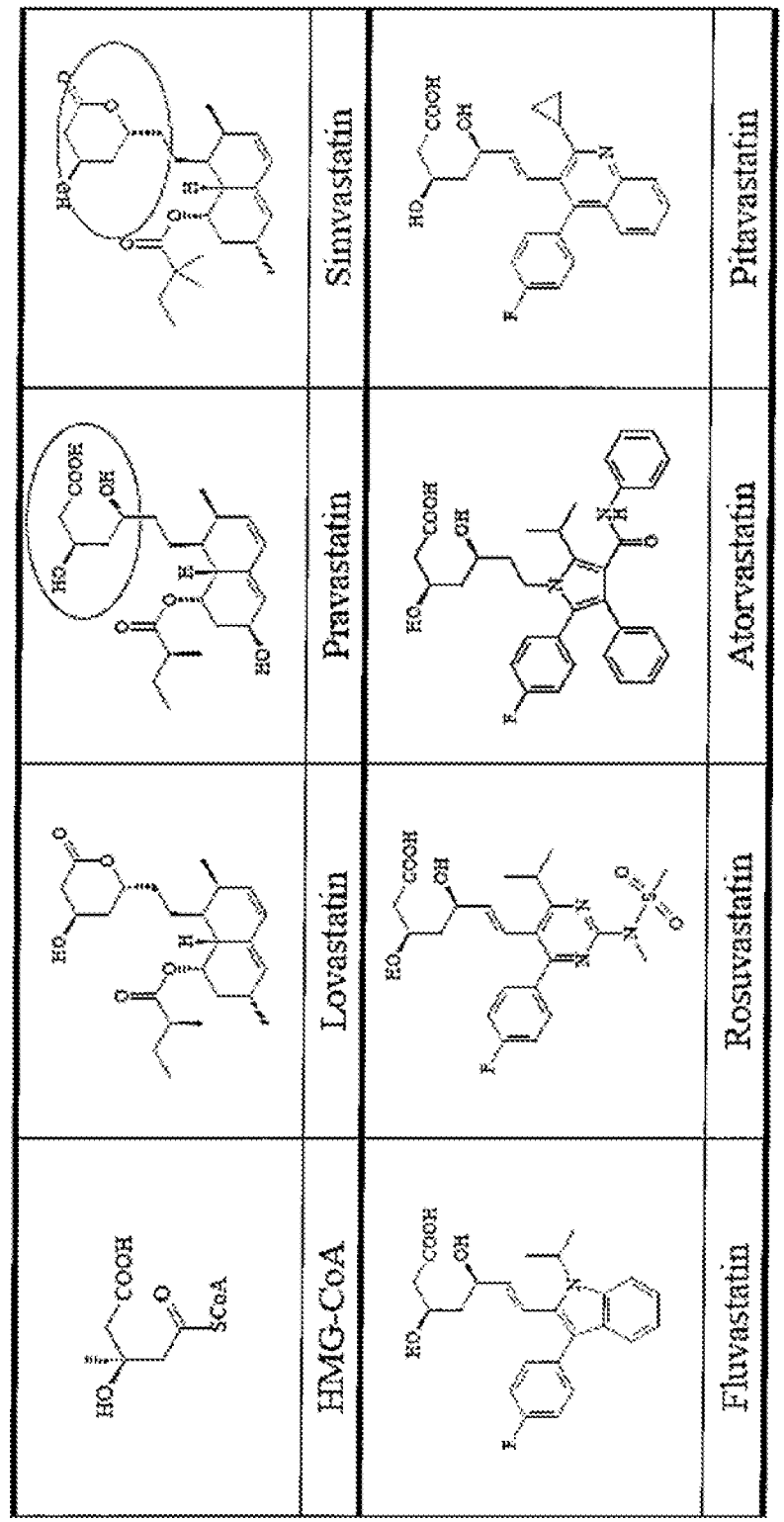
FIG. 2 shows the chemical structures of the statin drugs.
Figure 3:
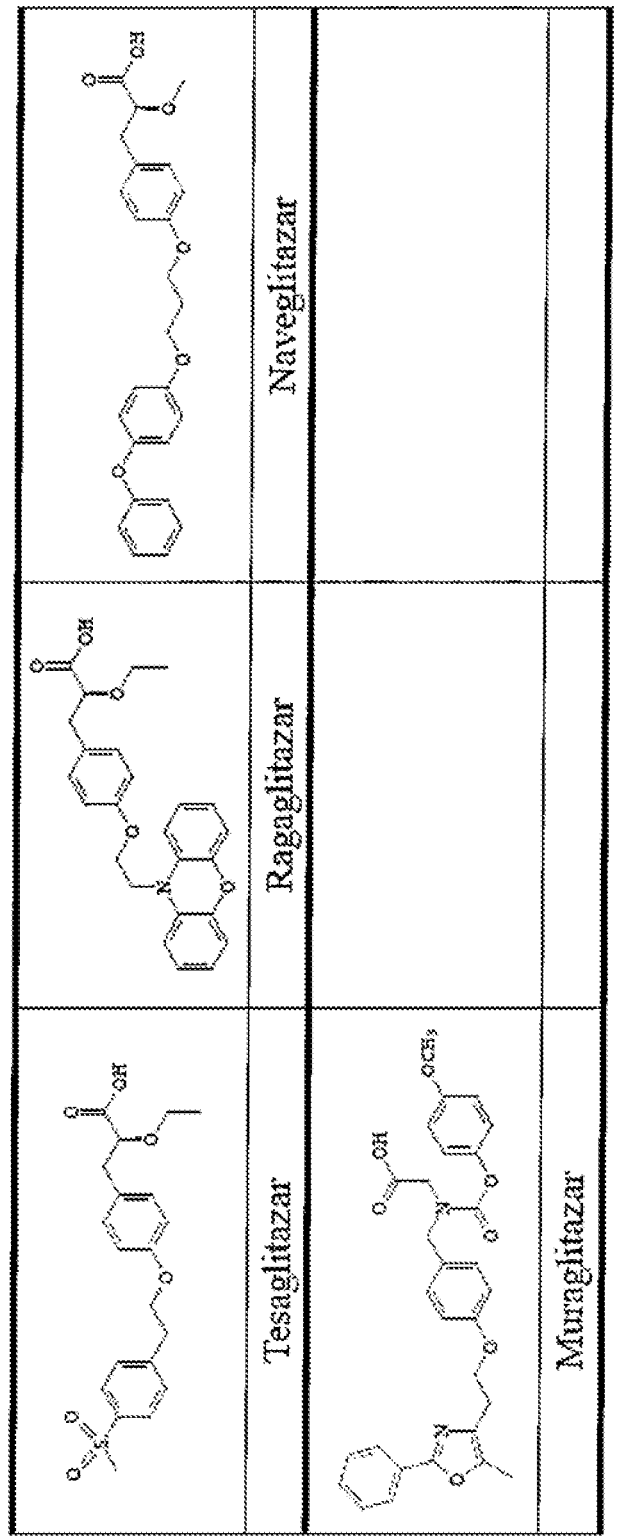
FIG. 3 shows the chemical structures of the PPAR dual agonist (alpha and gamma) drugs.

Unless otherwise defined herein, scientific and technical terms used in connection with the present invention shall have the meaning commonly understood by those of ordinary skill in the art. The meaning and scope of the terms should be clear; however, in the event of any latent ambiguity, definitions provided herein take precedence over any dictionary or extrinsic definition.

As utilized in accordance with the present disclosure, the following terms, unless otherwise indicated, shall be understood to have the following meanings.

The term "PPARγ modulators" as used herein refers to the agents that can modulate the expression or nuclear translocation of PPARγ.

The term "alkyl" as used herein refers to a saturated straight-chain or branched hydrocarbon group having 1 to 6 carbon atoms, especially 1 to 4 carbon groups, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl. $C_1$-$C_4$-alkyl means for example methyl, ethyl, propyl, 1-methylethyl, butyl, 1-methylpropyl, 2-methylpropyl or 1,1-dimethylethyl.

The term "heterocyclyl" as used herein refers to a monocyclic radical having 5 to 8 ring members, wherein in each case 1, 2, 3 or 4 of these ring members are heteroatoms selected, independently from each other, from the group consisting of oxygen, nitrogen and sulfur.

The term "preventing" or "prevention" as used herein refers to delaying the onset of the symptoms of a susceptible subject or reducing the occurrence of a disease.

The term "treating" or "treatment" as used herein denotes reducing and/or improving the symptoms of a susceptible subject or increasing the survival rate of the subject with certain lethal disorders or conditions.

The term "PPARγ-related disorders or conditions" as used herein denotes the disorders or conditions wherein the modulation of PPARγ is beneficial. For example, such disorders or conditions include insulin resistance, impaired glucose tolerance, Type II diabetes, obesity, hyperlipidemia, hypertension, angiocardiopathy, atherosclerosis, dyslipidemia, obesity and syndrome X, cardiovascular diseases, inflammation and neurology diseases, Alzheimer's disease, multiple sclerosis, Parkinson's disease, ischemic stroke, spinal cord injury, psoriatic arthritis, chronic obstructive pulmonary disease, eye diseases, viral infections, polycystic ovarian disease, inflammatory bowel disease, asthma, diseases of the bone, aging and longevity, drug metabolism, wound healing, acne, mitochondrial dysfunction diseases, ischemic stroke, renal diseases, liver diseases, lung diseases, cardiovascular diseases, autoimmune disorders, systemic inflammatory response syndrome (sepsis), and the like.

The term "subject" as used herein denotes animals, especially mammals. In one preferred embodiment, the term "subject" denotes humans. In another preferred embodiment, the term "subject" denotes companion animals, such as cats and dogs.

The term "therapeutically effective amount" as used herein refers to the amount of an active ingredient used alone or in combination with other treatments/medicaments for treating PPARγ-related disorders or conditions that show therapeutic efficacy.

The term "carrier," "pharmaceutically acceptable carrier," "cell-penetrating drug delivery system" or "pharmaceutically acceptable cell-penetrating drug delivery system" refers to particles that can encapsulate active pharmaceutical ingredients. Examples of cell-penetrating drug delivery systems suitable for the present invention include niosomes, polymersomes, nanoparticles, liposomes, nano suspended particles, solid lipid nanoparticles, magnetic nano-carriers, micelles, macromolecular conjugates, particulate drug carriers, and the like.

Unless otherwise required by context, singular terms shall include the plural and plural terms shall include the singular.

The inventors of the invention surprisingly found that compounds having a pyrimido[5,4-d]pyrimidine structure can enhance the expression and nuclear translocation of PPARγ, and thus may serve as novel types of PPARγ modulators. In a preferred embodiment, the pyrimido[5,4-d]pyrimidine compound is dipyridamole.

The present invention thus provides a method of preventing or treating PPARγ-related disorders or conditions, comprising administering to a subject in need thereof a therapeutically effective amount of a compound of formula (I):

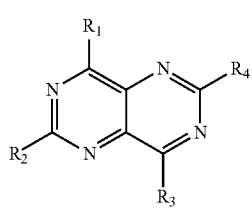

(I)

wherein each of $R_1$, $R_2$, $R_3$ and $R_4$ is independently selected from the group consisting of heterocyclyl and di(hydroxyalkyl)amino,
or a pharmaceutically acceptable salt thereof.

In an embodiment, $R_1$ and $R_3$ are heterocyclyl, preferably piperidyl, and $R_2$ and $R_4$ are di(hydroxyalkyl)amino, preferably N,N-di(hydroxyethyl)amino.

In a preferred embodiment, the compound is dipyridamole.

In another embodiment, the compound is encapsulated in a cell-penetrating drug delivery system, such as a niosome, a polymersome, a nanoparticle, a liposome, a nano suspended particle, a solid lipid nanoparticle, a magnetic nano-carrier, a micelle, a macromolecular conjugate or a particulate drug carrier.

In a preferred embodiment, the cell-penetrating drug delivery system is a liposome. In another embodiment, the liposome has a diameter in the range of about 100-300 nm, preferably about 150-280 nm, more preferably about 180-270 nm.

It is known in the art that when dipyridamole is administered in free form, it binds to the receptors on cell membrane and activates signaling pathways that cause unfavorable side effects. The inventors found that dipyridamole can promote PPARγ expression and nuclear translocation and thus activate the downstream signaling pathway. Activation of the PPARγ signaling pathway can facilitate the treatment of many diseases known to be associated with PPARγ inactivation.

Figure 4A:
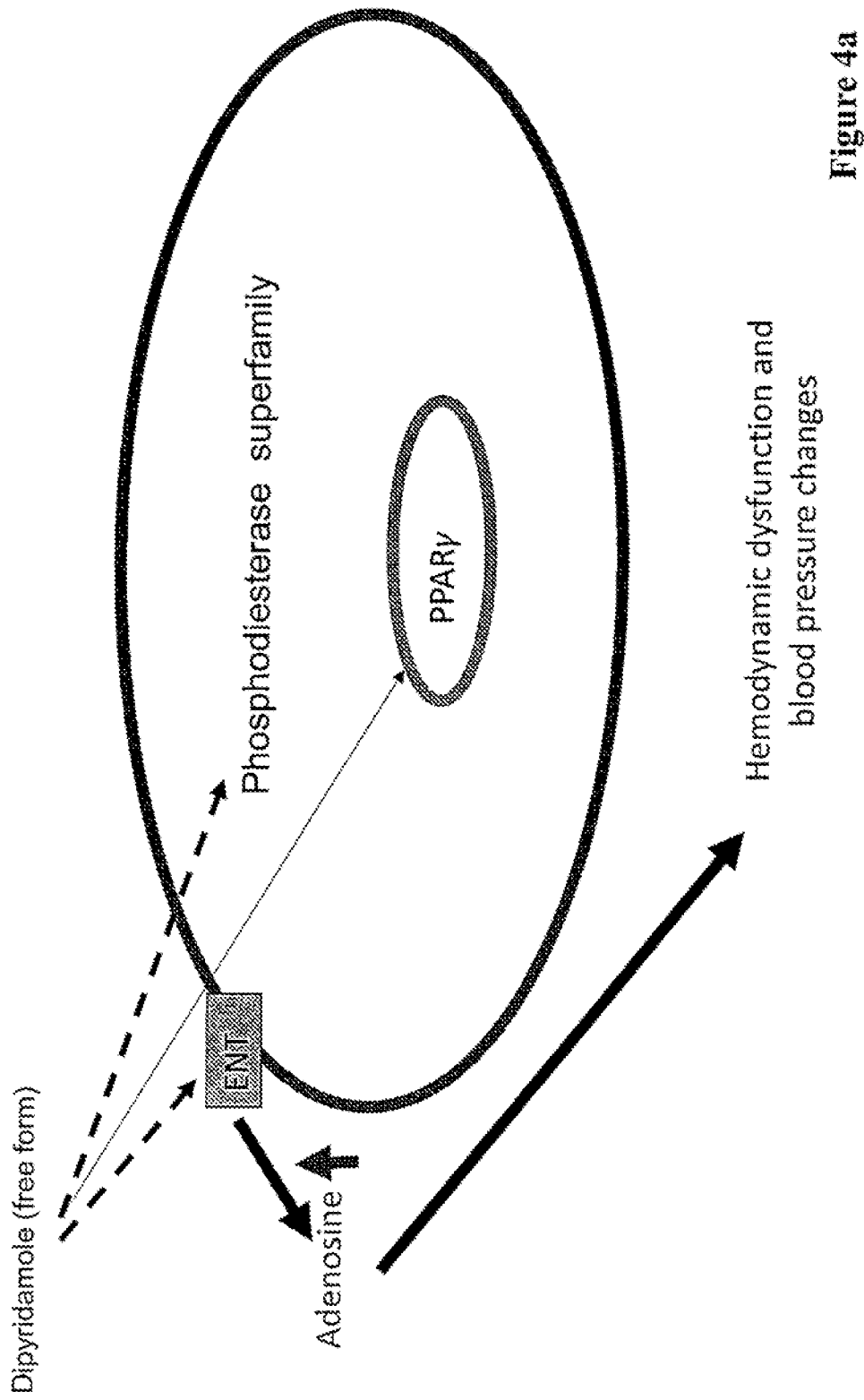
FIGS. 4a and 4b are schemes showing the action of dipyridamole when delivered in free form or in a cell-penetrating drug delivery system.
Figure 4B:
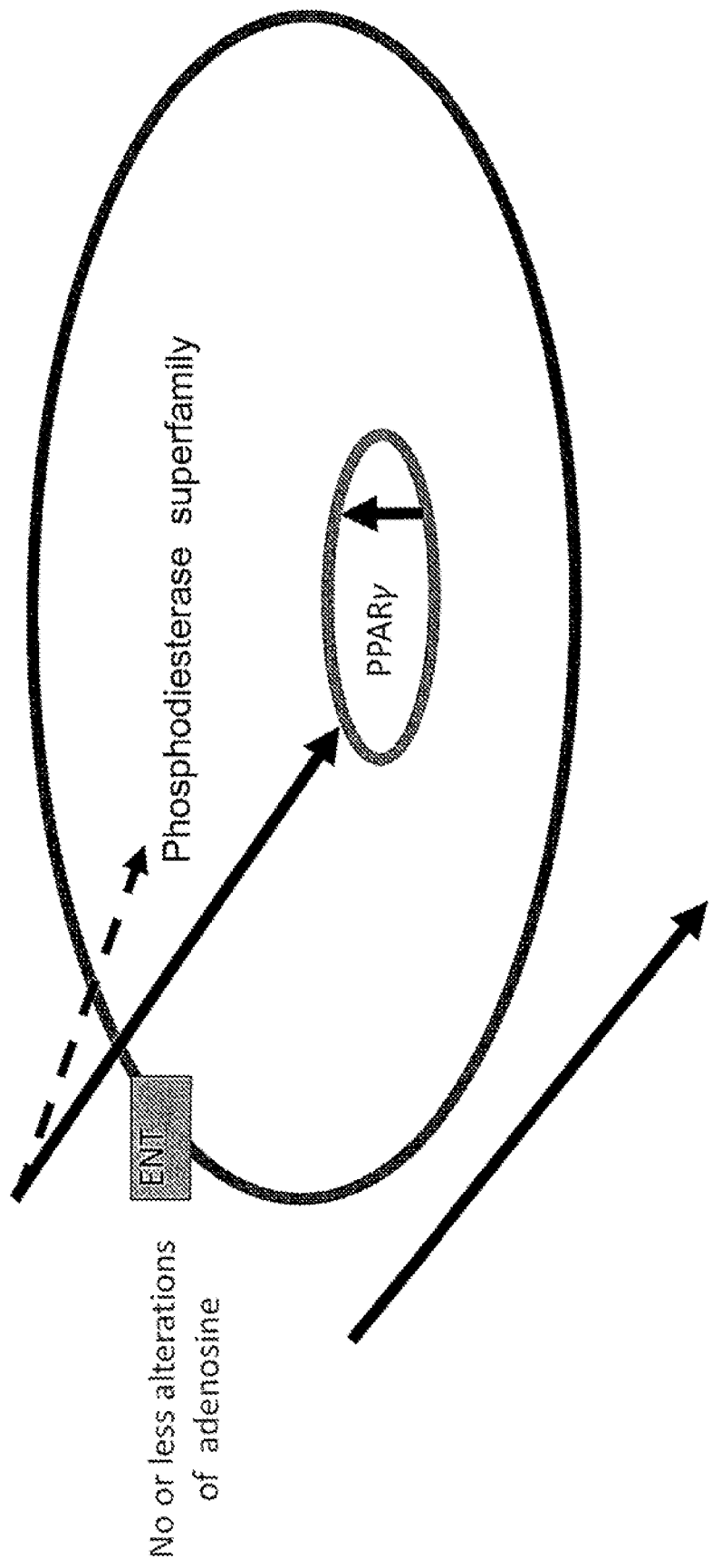

FIG. 4a shows that if dipyridamole is administered in free form, it mainly acts outside of cells and will promote the accumulation of adenosine, which will lead to hemodynamic dysfunction and blood pressure changes. FIG. 4b shows that dipyridamole inside the cell can activate the PPARγ signaling pathway, which can inhibit renal loss caused by LPS. In such case, the unfavorable action of dipyridamole outside the cell can be avoided. In the Examples below, the present invention demonstrates that by delivering dipyridamole directly into cells, the binding to the receptors on the cell membrane can be avoided so as to reduce side effects such as oxidative stress and vasoconstriction caused by the accumulation of adenosine.

The way nanoparticle drug carriers enter cells is different from that of conventional drugs. Conventional drugs enter cells by diffusion, which is dose-dependent. That is, the higher the drug concentration in the blood, the higher the drug concentration in the cells, and the drugs can only enter cytoplasm. Nanoparticle drug delivery systems are absorbed by cells through endocytosis and are lysosomotropic after entering cells. At the initial stage after injection, the concentration of the nanoparticle drug delivery systems increases in a time-dependent manner.

Endocytosis is a process to incorporate extracellular materials into cells. This process can be categorized into three types, i.e., phagocytosis, pinocytosis, and receptor-mediated endocytosis. Phagocytosis only occurs in specialized cells. These cells proliferate and aggregate upon stimulation by extracellular materials and engulf them into lysosomes in the cells for degradation. This process occurs in macrophages and neutrophils of the immune system. Pinocytosis is a process that internalizes extracellular fluid and molecules within it through the invagination of the cell membrane to form a pocket, which then pinches off into the cell to form a vesicle. The vesicle then travels into the cytosol and fuses with other vesicles such as endosomes and lysosomes.

Depending on the structure of the carriers, pinocytosis can be categorized into two types, fluid phase pinocytosis and adsorptive pinocytosis. If the carrier does not have a functional group that interacts with the cells, the cells will engulf the drug carrier by fluid phase pinocytosis. This process is slow and dependent on the carrier concentration around the cell membrane. Adsorptive pinocytosis occurs when the carrier has a hydrophobic group or is positively charged. Such carrier will be physically adsorbed by the cell membrane and increase the engulfing ability of the cells. The above two types of endocytosis are non-specific processes and are not suitable for delivery of drugs to their targets. Targeting can only be achieved in certain cancer tissues through enhanced permeability and retention (EPR).

Receptor-mediated endocytosis is a process by which cells absorb molecules (endocytosis) by the inward budding of plasma membrane vesicles containing proteins with receptor sites specific to the molecules being absorbed. After the drug carrier binds to the receptor on the cell, an intrinsic signal will trigger the cell membrane to form a coated pit. The surface area of a coated pit amounts to 1 to 2% of the cell membrane. The coated pit will detach from the cell membrane and enter into the cell to form coated vesicles in the cell, and subsequently form endosomes and move inside the cell in salutatory motion. An endosome is a complicated structure comprising microtubules and vesicles. The vesicles can fuse with Golgi. Due to the proton pump (ATPase), endosomes usually become acidic. The endosomes will then fuse with lysosomes to form secondary lysosomes.

The cell membrane is a barrier to be overcome for efficient delivery of therapeutics into a target site in mitochondria, cytoplasm or nucleus. The hydrophobic phospholipids are major components of the cell membrane that obstruct the transportation of therapeutics. Thus, various delivery systems, such as liposomes, nanoparticles and viral vectors, have been developed to transfer small molecules, peptides, proteins, and oligonucleotides across the membrane. Such manner of drug delivery is herein referred-to as cell-penetrating drug delivery systems.

A number of cell-penetrating drug delivery systems (liposomes, cell penetrating peptides, cationic polymer conjugates, and polymeric nanoparticles) have been explored for intracellular delivery of therapeutics. They need to be adapted to cross a series of membrane barriers in order to reach the site of drug action in the cells. During this process, a significant portion of the drug molecules will be lost at each successive barrier. These barriers include cellular association and internalization of the drug-carriers by endocytosis; intracellular trafficking and release of drug or drug-carrier into the cytoplasm; cytoplasmic translocation of drug or drug-carrier to nucleus or any other cellular organelle; and the nuclear/organellar uptake. Cells contain several intracellular organelles with specific functions. Intracellular targeting of therapeutics to these specific organelles is expected not only to significantly enhance the therapeutic efficacy but also reduce non-specific effects and hence toxicity. Therefore, there is significant interest in achieving intracellular target-specific delivery of therapeutics using different cell-penetrating drug delivery systems.

The cell-penetrating drug delivery systems that facilitate the endocytosis of drugs include nano-sized polymeric carriers and liposomes. Depending on the properties of the drugs and preparation processes, nano-sized drug carriers can be categorized into nanoparticles, nanoliposomes, nano suspended particles, solid lipid nanoparticles, magnetic nano-carriers, and the like.

In addition to the above-mentioned cell-penetrating drug delivery systems, cell-penetrating peptides (CPP), biodegradable nanoparticles, and viral vectors may also be used as delivery systems for enhancing the penetration of drugs into cells.

The cellular internalization of RGD peptides is primarily mediated by the clathrin, caveolae and macropinocytosis endocytic pathways at the plasma membrane. As one of the primary effectors of endocytic transport at the plasma membrane, clathrin-mediated endocytosis is involved in the transport of large extracellular particles into the cell through the receptor-dependent endocytosis of ligands. An alternative route for peptide internalization is through caveolae-mediated endocytosis. Internalization through this pathway is facilitated by lipid rafts in the cell membrane; these rafts contain caveolin-1 proteins that form endosomes, which are then transported throughout the cell. In contrast, macropinocytosis involves the fluid-phase endocytosis of small extracellular particles into the cell. It has been demonstrated that the $\alpha V\beta 3$ integrin can be internalized through both the clathrin and caveolae-dependent endocytic pathways as part of the regulation of integrin turnover. Therefore, RGD peptides are ideal for cell penetrating drug delivery system (Cam A, Sivaguru M, Gonzalez de Mejia E. Endocytic mechanism of internalization of dietary peptide lunasin into macrophages in inflammatory condition associated with cardiovascular disease. PLoS One. 2013 Sep. 5; 8(9): e72115).

As the cell membrane constitutes a major barrier for intracellular delivery of large-sized hydrophilic proteins, peptides and oligonucleotides, cell penetrating peptides (CPPs) have been explored to overcome this barrier. These CPPs can ferry molecules or colloidal drug delivery systems that are tagged to them across the cell membrane, into the cytoplasm and to the nucleus. The characteristics of CPPs are attributed to the presence of a stretch of 9-16 cationic amino acid residues; the most commonly studied CPPs include HIV-1 transactivating transcriptional activator (TAT) peptide, HSV VP-22 (Herpes Simplex virus type-1 transcription factor) peptide and penetratin. Several theories have been proposed to determine the exact mechanism by which these CPPs enter the cells. For example, TAT penetration through cell membrane has been shown to be independent of receptors and transporters, and has been suggested to enter the cell by forming an inverted micelle by destabilizing the phospholipid bilayer. The main benefit of TAT coupling is that, along with efficient delivery of molecules, biological activity of the coupled molecule is preserved, and the size of the molecule being transported is also not a rate-limiting factor.

TAT has been suggested not only to enhance intracellular delivery, but also nuclear delivery, and hence has been investigated for nucleic acid delivery. TAT peptide conjugated to antisense oligonucleotide has been shown to deliver oligonucleotides to the nucleus. After being internalized, TAT peptide has also been found to co-localize inside the Golgi body along with BODIPY-ceramide, which is a marker for Golgi body. Therefore, it is quite possible that there is direct trafficking from the early endosome to the Golgi body without entering the late endosome. A secretory pathway could be present where the peptide enters the cytosol from the endoplasmic reticulum. Gene therapy has demonstrated a significant potential in the treatment of genetic, acquired and neurodegenerative disorders. Amongst non-viral gene delivery methods, various drug delivery systems and polymers are being investigated such as liposomes, cationic lipid-DNA, polymer complexes. To overcome relatively inefficient cellular uptake of non-viral gene expression vectors, TAT peptide conjugation to vectors has been explored.

Kleeman et al. have demonstrated gene expression in alveolar basal epithelial cells with polyethylenimine (PEI) covalently coupled to TAT through a polyethylene glycol (PEG) spacer which demonstrated higher transfection efficiencies in vivo in mice lung following intratracheal administration than unconjugated PEG complex. In a similar study by Rudolph et al., solid lipid particles conjugated to dimeric HIV-1 TAT demonstrated enhanced gene delivery to the lungs.

CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs comprises the hydrophobic peptides, containing only apolar residues, with low net charge or hydrophobic amino acid groups that are crucial for cellular uptake. Among the cell-penetrating peptides, the arginine-rich cell-penetrating peptides have been the most widely studied. Examples include the TAT peptide from the HIV transactivator protein TAT, Penetratin, a 16 amino acid domain from the Antennapedia protein of *Drosophila*, a flock house virus (FHV) coat peptide (sequence 35-49), and oligoarginines.

Biodegradable nanoparticle-mediated intracellular delivery is a dynamic process; involving endocytosis, exocytosis, and sorting into different intracellular compartments. It appears that the NP surface and its interaction with cell surface controls the uptake and intracellular trafficking of biodegradable nanoparticles, and hence that of the encapsulated therapeutic agents.

Viral vectors are tools commonly used by molecular biologists to deliver genetic materials into cells. This process can be performed inside a living organism (in vivo) or in cell culture (in vitro). Hence, viral vectors are applicable options for use in cell-penetrating drug delivery systems.

Cell-penetrating peptides and biodegradable nanoparticles can be used not only to modify drugs but also be conjugated to carries to enhance the transmembrane effects.

Dipyridamole is an equilibrative nucleoside transporter (ENT) inhibitor. Nucleoside transporters (NTs) play an essential role in the transport of nucleosides across cellular membranes. Dipyridamole blocks the equilibrative nucleoside transporter (ENT), which facilitates the transmembranous diffusion of adenosine. Dipyridamole will increase the extracellular endogenous adenosine concentration, mainly in situations of increased extracellular formation of adenosine, such as occurs during hypoxia or inflammation. However, the extracellular endogenous adenosine concentration induced by dipyridamole causes vasodilatation, which contributes to the metabolic control of organ perfusion. Dipyridamole stress myocardial imaging is a successful, widely used technique for diagnosing and evaluating coronary artery disease. Coronary vasodilation with IV dipyridamole is associated with significant reductions in blood flow to collateral-dependent myocardium consistent with coronary steal in patients with CAD. In addition, there have been further studies that discovered vasoconstrictor and vasodilator effects of dipyridamole in many organs, including kidney, lung, pancreas, brain and so on.

Dipyridamole not only causes vasoconstriction in some organs but can also lead to low blood pressure and subsequent side effects such as vertigo and palpitations due to dilation of blood vessels of the heart. The effect of reducing blood pressure makes dipyridamole unsuitable for the treatment of patients who are physiologically unstable, such as those having, but not limited to, sepsis, ischemic stroke, hemorrhagic stroke, acute lung injury, acute liver injury, myocardium infarct, and cardiorenal syndrome. Furthermore, the blood-flow restricting effect of dipyridamole limits its application in the treatment of diseases involving organs rich with blood vessels.

Since the pharmacological action of dipyridamole is mainly on cell membranes, a delivery system designed for membrane penetration that avoids binding with equilibrative nucleoside transporter on the membrane while enhancing the intracellular signal transduction and PPARγ regulation can prevent the effect of tissue hypoperfusion due to increased cardiovascular dilation and local blood flow restriction. The limitation in clinical applications of dipyridamole in acute and severe patients due to the decrease of blood pressure can thus be lifted.

Dipyridamole is also a non-selective phosphodiesterase inhibitor. Increase of intracellular drug delivery will enhance the inhibition of dipyridamole on intracellular PDE. Members of the PDE family have unique cell- and tissue-specific distribution. Dipyridamole may be used as anti-inflammatory, anti-oxidant, anti-fibrosis, and smooth muscle relaxing agents for treating diseases associated with PDE regulation depending on the distribution profile of PDE on cell membranes or in cytoplasm in different tissues.

The unique cell- and tissue-specific distribution of PDEs are shown in the below table (see US 2012/0065165):

| PDE Isoenzyme | Substrate | Tissue Expression |
| --- | --- | --- |
| 1 | $Ca^{2+}$/calmodulin-stimulated | Heart, brain, lung, smooth muscle |
| 2 | cGMP-stimulated | Adrenal gland, heart, lung, liver, platelets |
| 3 | cGMP-inhibited | Heart, lung, liver, platelets, adipose tissue, inflammatory cells |
| 4 | cAMP-selective | Sertoli cells, kidney, brain, liver, lung, inflammatory cells |
| 5 | cGMP-specific | Lung, platelets, vascular smooth muscle, heart |
| 6 | cGMP-specific | Photoreceptor |
| 7 | cAMP-specific, high affinity | Skeletal muscle, heart, kidney, brain, pancreas, T lymphocytes |
| 8 | cAMP-selective | Testes, eye, liver, skeletal muscle, heart, kidney, ovary, brain, T lymphocytes |
| 9 | cGMP-specific | Kidney, liver, lung, brain, possibly heart |
| 10 | cGNO-sensitive, cAMP-selective | Testes, brain |
| 11 | cGMP-sensitive, dual specficity | Skeletal muscle, prostate, kidney, liver, pituitary and salivary glands, testes |

Increase in the capability of dipyridamole to penetrate the membrane can facilitate the inhibition of PDE3, PDE5 and PDE8 in specific tissues and confer dipyridamole therapeutic efficacy in diseases associated with PDE3, PDE5 and PDE8. In such case, dipyridamole may be used for treating lower urinary tract dysfunction and erectile dysfunction, like other PDE5 inhibitors. Furthermore, since dipyridamole is a non-selective PDE inhibitor, it may be used for the treatment of PDE associated diseases when delivered by a transmembrane drug delivery system.

In an embodiment, the compound of formula (I) of the invention is encapsulated in a cell-penetrating drug delivery system for delivery into the cell. In a preferred embodiment, the cell-penetrating drug delivery system is a niosome, a polymersome, a nanoparticle, a liposome, a nano suspended particle, a solid lipid nanoparticle, a magnetic nano-carrier, a micelle, a macromolecular conjugate or a particulate drug carrier. Preferably, the cell-penetrating drug delivery system is a liposome. The liposome suitable for the present invention has a diameter in the range of about 100-300 nm, preferably about 150-280 nm, more preferably about 180-270 nm.

In another embodiment of the invention, the cell-penetrating drug delivery systems may be niosomes, polymersomes, or polymers that have a diameter of less than 1 μm. Modifications can be made based on surface electric potential, hydrophilicity/hydrophobicity, size, morphology, shape and/or surface curvature.

The liposome formulation of the invention may comprise vesicles of various nature (e.g., unilamellar or multilamellar), composition, size, and characteristics, enclosing an aqueous medium of diverse composition, pH and osmotic strength. In a preferred embodiment, the main constituents of the liposome lipid layer membrane are selected from the group consisting of natural or synthetic phospholipids such as those listed below:

1,2-Dilauroyl-sn-Glycero-3-Phosphocholine (DLPC)
1,2-Dimyristoyl-sn-Glycero-3-Phosphocholine (DMPC)
1,2-Dipalmitoyl-sn-Glycero-3-Phosphocholine (DPPC)
1,2-Distearoyl-sn-Glycero-3-Phosphocholine (DSPC)
1,2-Dioleoyl-sn-Glycero-3-Phosphocholine (DOPC)
1,2-Dimyristoyl-sn-Glycero-3-Phosphoelhanolamine (DMPE)
1,2-Dipalmitoyl-sn-Glycero-3-Phosphoelhanolamine (DPPE)
1,2-Distearoyl-sn-Glycero-3-Phosphoelhanolamine (DSPE)
1,2-Dioleoyl-sn-Glycero-3-Phosphoelhanolamine (DOPE)
1-Myristoyl-2-Palmitoyl-sn-Glycero-3-Phosphocholine (MPPC)
1-Palmitoyl-2-Myristoyl-sn-Glycero-3-Phosphocholine (PMPC)
1-Stearoyl-2-Palmitoyl-sn-Glycero-3-Phosphocholine (SPPC)
1-Palmitoyl-2-Stearoyl-sn-Glycero-3-Phosphocholine (PSPC)
1,2-Dimyristoyl-sn-Glycero-3-[Phospho-rac-(1-glycerol)] (DMPG)
1,2-Dipalmitoyl-sn-Glycero-3-[Phospho-rac-(1-glycerol)] (DPPG)
1,2-Distearoyl-s/i-Glycero-3-[Phospho-rac-(1-glycerol)] (DSPG)
1,2-Dioleoyl-sn-Glycero-3-[Phospho-rac-(1-glycerol)] (DOPG)
1,2-Dimyristoyl-sn-Glycero-3-Phosphate (DMPA)
1,2-Dipalmitoyl-sn-Glycero-3-Phosphate (DPPA)
1,2-Dipalmitoyl-sn-Glycero-3-[Phospho-L-Serine] (DPPS)
phosphatidylserine (PS), and
Natural L-a-phosphatidylcholine (from chicken egg, EPC, or from soy, SPC and HSPC).

Preferred phospholipids are long saturated phospholipids, e.g. those having alkyl chains of more than 12, preferably more than 14, more preferably more than 16, most preferably more than 18 carbon atoms.

Preferred liposome compositions for use according to the invention are preferably those in which the liposomes are uni- and/or multilamellar, and comprise:
(i) 1 to 100, preferably 40 to 70 mol % physiologically acceptable phospholipids, preferably selected from the group consisting of DLPC, DMPC, DPPC, DSPC, DOPC, DMPE, DPPE, DSPE, DOPE, MPPC, PMPC, SPPC, PSPC, DMPG, DPPG, DSPG, DOPG, DMPA, DPPA, DPPS, PS, EPC, SPC and HSPC.
(ii) 1 to 100, preferably 40 to 70 mol % sphingolipids, preferably sphingomyelin;
(iii) 1 to 100, preferably 40 to 70 mol % surfactants, preferably featuring hydrophobic alkyl ethers (e.g. Brij), alkyl esters, polysorbates, sorbitan esters, and/or alkyl amides;
(iv) 5 to 100, preferably 50 to 100 mol % amphiphilic polymers and/or co-polymers, preferably block copolymers comprising at least one block of a hydrophilic polymer or copolymer such as polyethylene glycol, and at least one block of a hydrophobic polymer or copolymer such as poly(lactide), poly(caprolactone), poly(butylene oxide), poly(styrene oxide), poly(styrene), poly(ethylethylene), or polydimethylsiloxanes,
(v) 0 to 60 mol %, preferably 20 to 50 mol % toxin retention-enhancing compounds, preferably sterol derivatives, preferably cholesterol, or
(vi) 0 to 30 mol %, preferably 1 to 5 mol % steric stabilizers, preferably PEGylated compounds, preferably PEGylated lipids, more preferably DSPE-PEG.

In a preferred embodiment, liposome-like vesicles are made from polymers and comprise no lipids, for which reason they are formally not considered liposomes but are called polymersomes. However, for the purpose of the present invention, polymersomes are meant to be encompassed by the term liposome as used for defining the invention and the claims.

Similarly, liposome-like vesicles made from synthetic surfactants and comprising no lipids are called niosomes. However, for the purpose of the present invention, niosomes are meant to be encompassed by the term liposome as used for defining the invention and the claims.

In an embodiment of the invention, polymerization of different high molecular polymers can be used, which comprise those in tri-block copolymer form such as ABA and BAB, and those in block copolymer form such as PLLA-PEG, PLGA-PEG, PLA-PEG, PLLA-mPEG, PLGA-mPEG and PLA-mPEG. Various shapes such as asterisk and L form can be designed, including block copolymers of PEG-(PLGA)$_8$, PEG-(PLLA)$_8$ and PEG-(PDLA)$_8$ Star. PEGylated modification can be used to modify any vehicle such as polymeric vehicle and liposome to achieve the effect of reducing the binding rate of plasma proteins (see Park, J. et al., (2009) "PEGylated PLGA nanoparticles for the improved delivery of doxorubicin. Nanomedicine." 5(4):410-418; Lück, M. et al., (1998) "Plasma protein adsorption on biodegradable microspheres consisting of poly(D,L-lactide-co-glycolide), poly(L-lactide) or ABA triblock copolymers containing poly(oxyethylene). Influence of production method and polymer composition." J. Control Release. 55(2-3):107-20; and Sempf, K. et al, (2013) "Adsorption of plasma proteins on uncoated PLGA nanoparticles." Eur. J. Pharm. Biopharm. 85(1):53-60).

The animal dose should not be extrapolated to a human equivalent dose (HED) by a simple conversion based on body weight. The Food and Drug Administration has suggested that the extrapolation of animal dose to human dose is correctly performed only through normalization to BSA, often represented in mg/m$^2$. The human dose equivalent can be more appropriately calculated using the formula: HED (mg/kg)=Animal dose (mg/kg) multiplied by Animal Km/Human Km. To convert the dose used in a mouse to a dose based on surface area for humans, multiply 22.4 mg/kg (Baur's mouse dose) by the Km factor (3) for a mouse and then divide by the Km factor (37) for a human (see below Table).

| Values based on data from FDA Draft Guidelines | | | |
|---|---|---|---|
| Species | Weight (kg) | BSA (m$^2$) | $K_m$ factor |
| Human Adult | 60 | 1.6 | 37 |
| Child | 20 | 0.8 | 25 |
| Baboon | 12 | 0.6 | 20 |
| Dog | 10 | 0.5 | 20 |
| Cat | 2.5 | 0.2 | 12.5 |
| Monkey | 3 | 0.24 | 12 |
| Rabbit | 1.8 | 0.15 | 12 |
| Guinea pig | 0.4 | 0.05 | 8 |
| Rat | 0.15 | 0.025 | 6 |
| Hamster | 0.08 | 0.02 | 5 |
| Mouse | 0.02 | 0.007 | 3 |

To convert a dose expressed in mg/kg to dose in mg/m$^2$, multiply by $K_m$ value. According to the present invention, the effective dose of liposome-dipyridamole in mice is 10 mg/kg-100 mg/kg, in hamsters 6-60 mg/kg, in rats 5-50 mg/kg, in guinea pigs 3.75-37.5 mg/kg, in rabbits 2.5-25 mg/kg, in monkeys 2.5-25 mg/kg, in dogs 1.5-15 mg/kg, in cats 2.4-24 mg/kg, in baboons 1.5-15 mg/kg, in children 1.2-12 mg/kg, and in adults 0.81-8.1 mg/kg. Taking into consideration the differences in drug sensitivity among species, the broadest dose range without limiting the species is 0.4-160 mg/kg, preferably 0.6-120 mg/kg, more preferably 0.8 mg/kg-100 mg/kg.

Having now generally described the invention, the same may be more readily understood through reference to the following examples, which provide exemplary protocols for the production of the pharmaceutical composition of the invention and its use in the enhancement of the treatment of acute stroke. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXAMPLES

Example 1: Preparation of Dipyridamole Liposome

Figure 5:
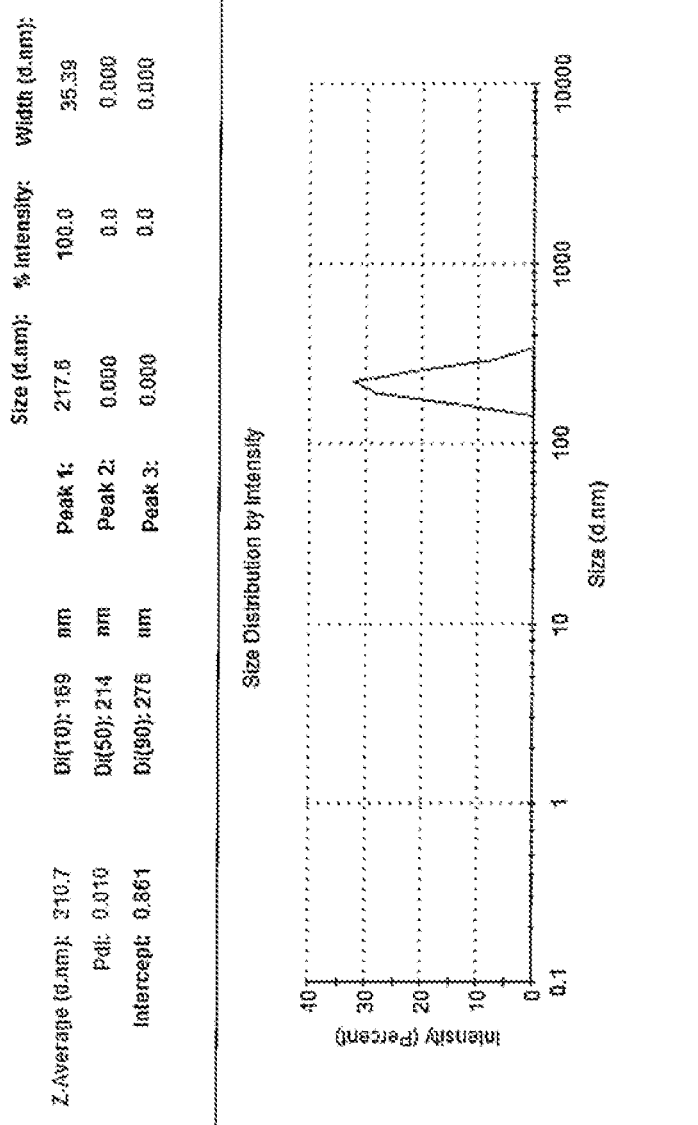
FIG. 5 shows the data of the diameters of the liposomes.
Figure 6:
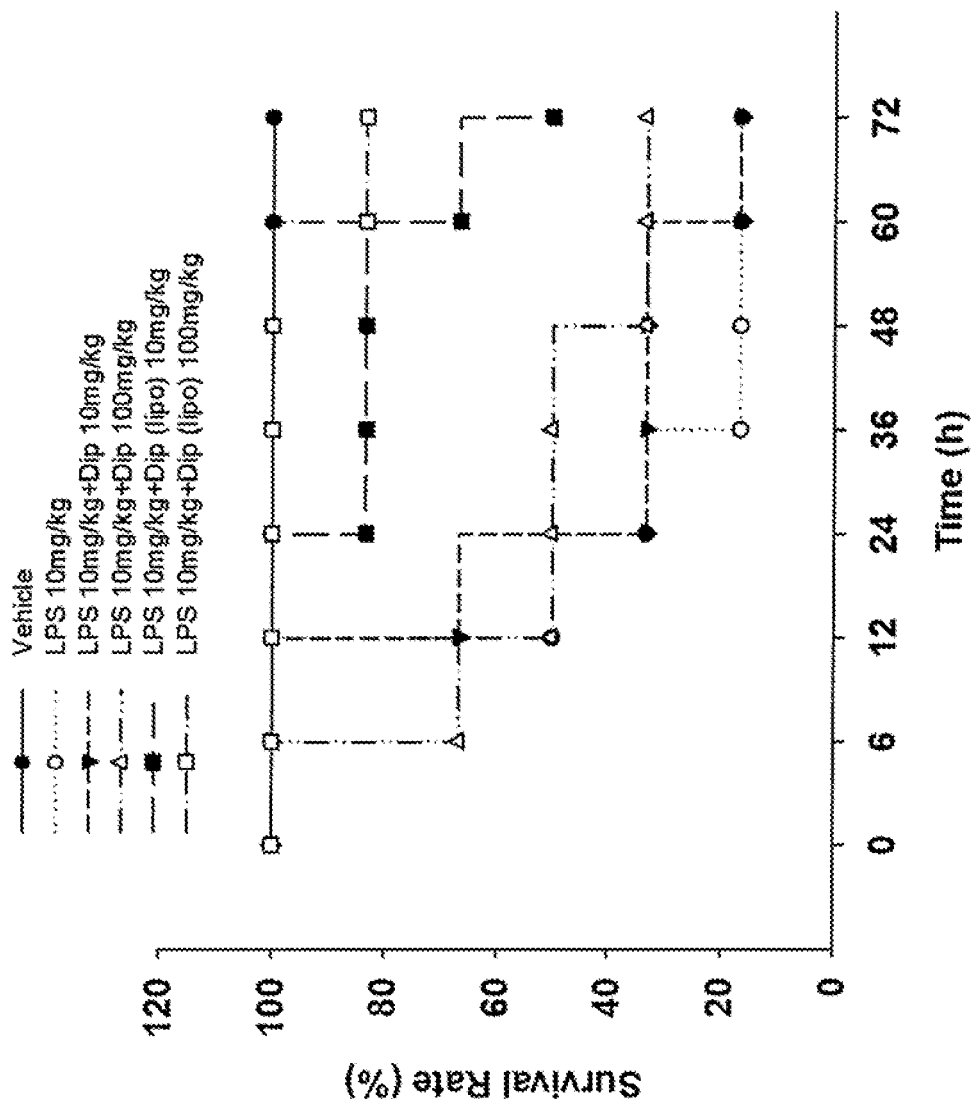
FIG. 6 shows survival rate of mice with LPS-induced sepsis after treatment.

Liposomes were prepared with positive and neutral charge containing phospholipid and cholesterol, in which the mole percent of cholesterol was 5% to 75%, either with or without PEG2000-DSPE at 5 mol % to phospholipids. Small unilamellar vesicles were prepared. The dried lipid films were hydrated with ammonium sulfate and sequentially extruded through a series of polycarbonate membrane filters. Dipyridamole was encapsulated into the liposomes via a transmembrane pH gradient or dehydration-rehydration, and the diameters of the extruded liposomes were in the range of 100-350 nm. The diameter of the liposome-dipyridamole was about 169 to 276 nm as shown in FIG. 5.

Example 2: HEK293 Cells Treated with the Dipyridamole Liposome

Example 2.1: Expression of PPARγ in Cells Treated with the Dipyridamole Liposome The cell line used in the assay was human embryonic kidney cells, HEK293. The cells were treated with the agents shown in Table 1 below.

TABLE 1

| Experimental Design | | | | | | |
|---|---|---|---|---|---|---|
| | Groups | | | | | |
| | 1 | 2 | 3 | 4 | 5 | 6 |
| Treatments | None | 100 ng/mL LPS | LPS 6 h+ Dipyridamole 10 ug/mL (Free form) 2 h | LPS 6 h+ Dipyridamole 100 ug/mL (Free form) 2 h | LPS 6 h+ Dipyridamole 10 ug/mL (Liposome) 2 h | LPS 6 h+ Dipyridamole 100 ug/mL (Liposome) 2 h |

The cells were collected at 0 h, 3 h and 12 h after treatment. The collected cells were washed with 150 μL Buffer A (10 mM Hepes pH=7.9, 1.5 mM MgCl$_2$, 10 mM KCl, 1.0 mM DTT, 0.1% Triton-X 100), and centrifuged at 3000 g for 10 minutes at 4° C. Supernatant containing cytosolic proteins was collected, and the pellets were re-suspended with 50 μL Buffer B (20 mM Hepes pH=7.9, 1.5 mM MgCl$_2$, 0.42M NaCl, 1.0 mM DTT, 1.0M PMSF, 0.2 mM EDTA) and incubated on ice for 30 minutes followed by centrifuging at 12000 g for 10 minutes at 4° C. Supernatant containing nucleic proteins was then collected, and the expression of P65 protein, which is indicative of the activation of PPARγ, was analyzed using Western blotting. The method is as follows:

Protein concentration was measured using Bradford assay. 6× sample buffer (0.8 mM Tris-HCl, 10 mM EDTA, 10% SDS, 60% glycerol, 0.6 M β-mercaptoethano, 0.06% bromophenol blue, pH 6.8) was added into 50 μg of nuclear proteins and an equal volume of lysis buffer was added into the samples. After being heated at 95° C. for 10 minutes to denature the proteins, the samples were immediately cooled on ice.

Figure 7A:
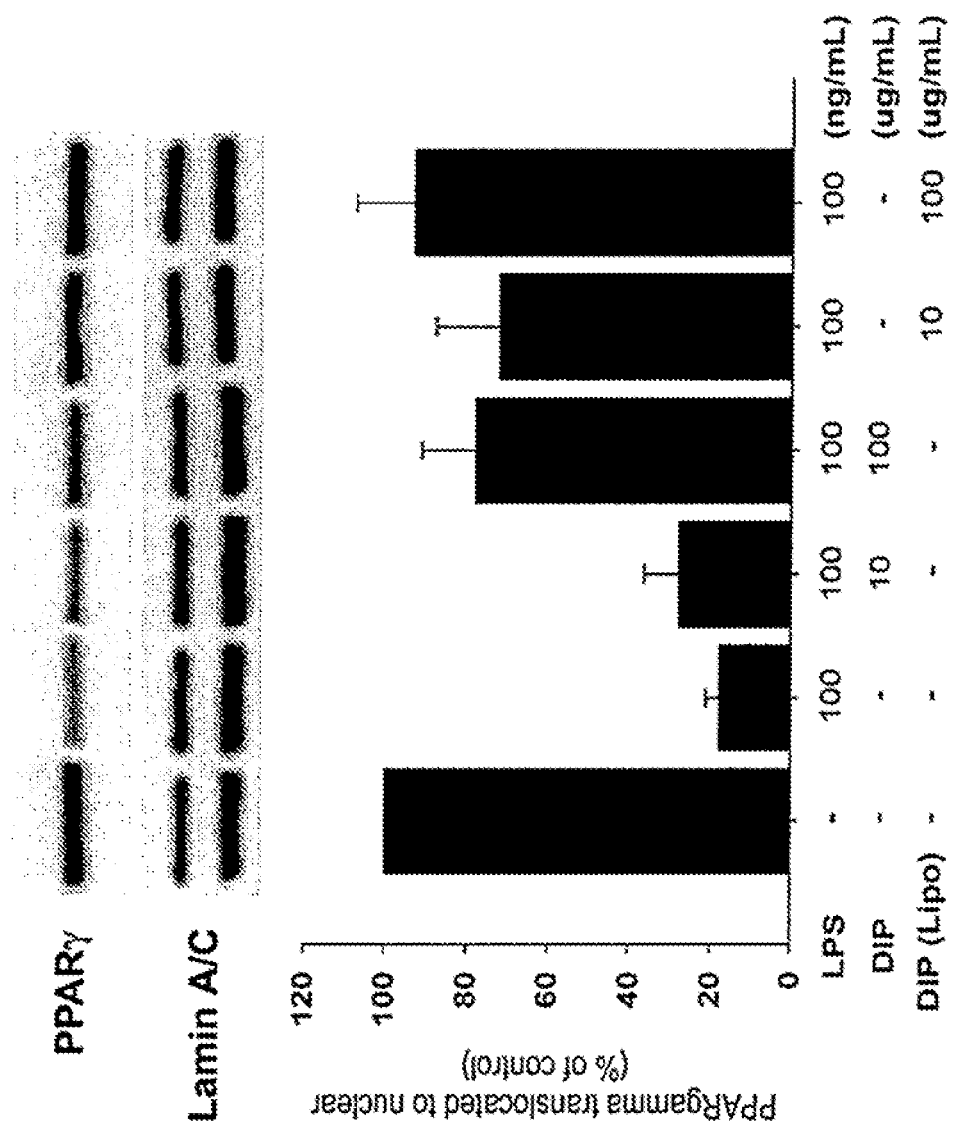
FIGS. 7a and 7b show the expression of PPARγ in HEK293 cells treated with the dipyridamole (free form) and dipyridamole liposome.
Figure 7B:
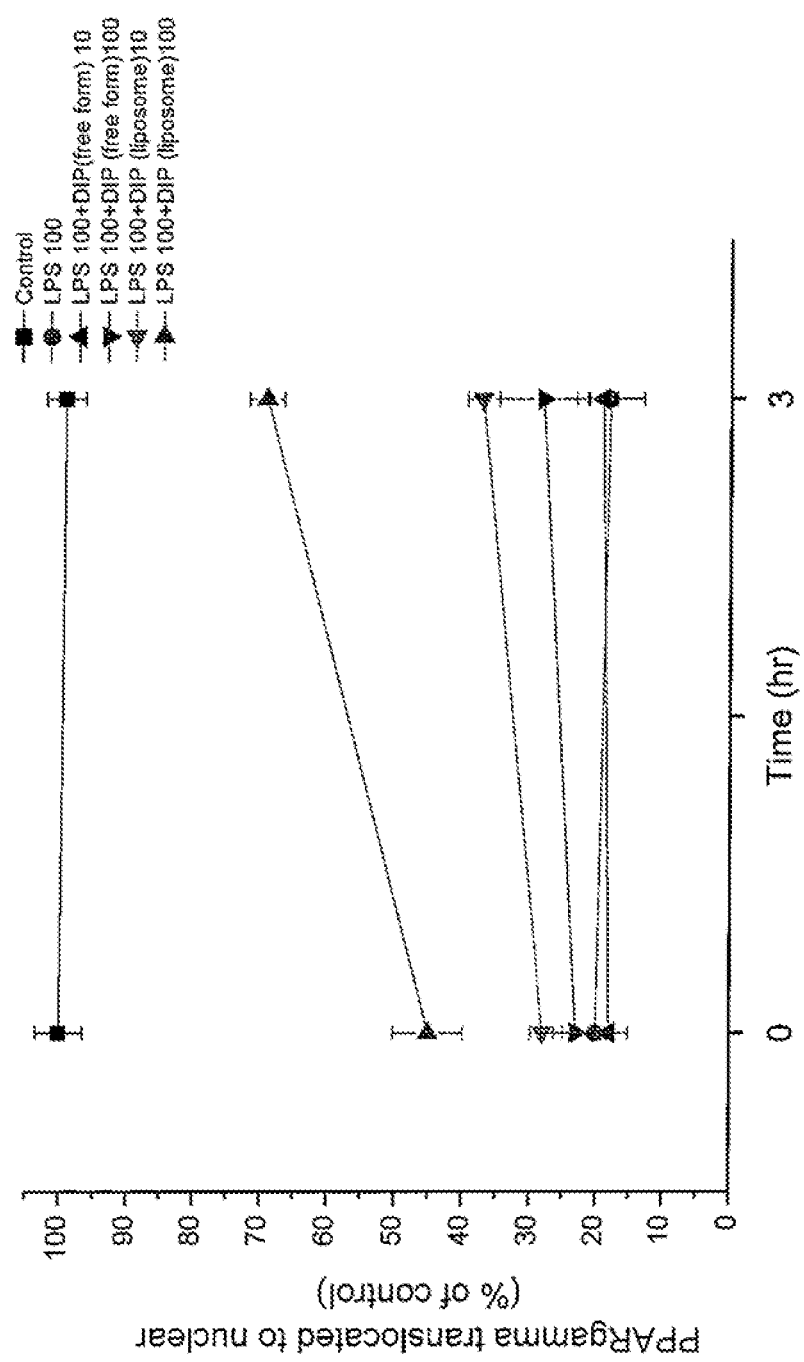

The samples were then separated by 10% SDS-PAGE electrophoresis (100 V) and transferred from the SDS-PAGE gels to PVDF membranes by wet blotting. The PVDF membranes were then treated with 5% skimmed milk at room temperature for 60 minutes to block non-specific binding. The membranes were incubated with primary antibody overnight at 4° C. and washed three times with PBST. The membranes were incubated with secondary antibody at room temperature for 60 minutes and washed three times with PBST. The membranes were then washed one more time with PBS and incubated with an enhanced chemiluminescence (ECL) substrate for detection. Photos of the images were taken using automated chemiluminescence and fluorescence imaging system (UVP Biospectrum). The expression of PPARγ in the testing groups relative to the control group is shown in FIG. 7a (12 hour) and FIG. 7b (0 and 3 hour).

The primary antibodies used in this experiment is rabbit anti-human PPARγ antibody (1:1000) (catalog no.: 07-466), MILLIPORE; and rabbit anti-human Lamin A/C (1:1000) (catalog no.: GTX62457), GeneTex. The secondary antibody used in this experiment is mouse anti-rabbit HRP (1:3000) (ab6721), sigma.

Example 2.2: Viability of Cells Treated with the Dipyridamole Liposome

Figure 8:
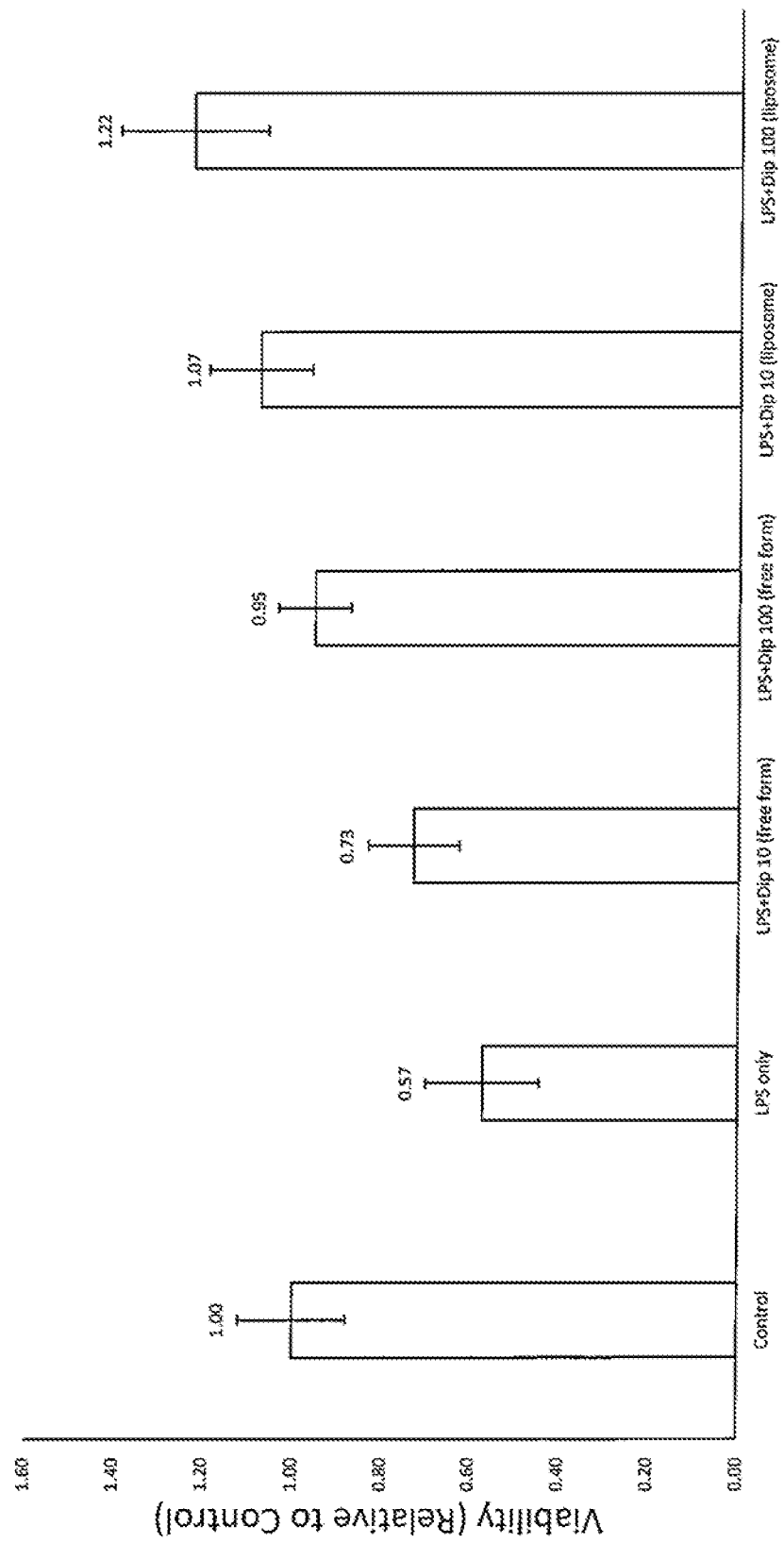
FIG. 8 shows viability of HEK293 cells treated with dipyridamole (free form) and dipyridamole liposome.

The number of viable cells was evaluated 24 hours after initial treatment using the Cell Counting Kit-8 (Dojindo Laboratories, Japan) following the manufacturer's instructions, and the optical absorbance at wavelength 450 nm was measured for the supernatant of each well using the plate reader Multiskan EX (Thermo Fisher Scientific Inc., Waltham, MA). The data are shown in FIG. 8.

Example 3: Survival Rate Analysis in Mice with LPS-Induced Sepsis

Male C57Bl/6J mice, 8-12 weeks of age, were used in this study. They were reared in an air-conditioned environment with 6 am to 18 pm light cycle and fed standard rodent chow ad libitum. LPS (*Escherichia coli* 0111:B4) (SigmaAldrich, Milwaukee, WI, USA) was freshly dissolved in sterile pyrogen-free water each time when applied. First, mice were injected intraperitoneally with LPS (16 mg/kg) and followed for 72 hours to observe the survival rate. The dose of LPS was determined by preliminary experiments that demonstrated longer survival than 24 hours in half of the animals injected. Dipyridamole was administered 1 hour after the LPS treatment.

Example 4: Detection of Biomarkers in Plasma 4.1: Liver Markers (AST, ALT) and Kidney Markers (BUN, Creatinine)

Blood samples for biochemical measurements were collected from each animal before and at 24 hours into the experiment. Samples were separated by centrifugation, and the serum was stored at −80° C. until analysis. Serum total cholesterol was measured using Merck assay kits (Darmstadt, Germany). Serum blood urea nitrogen (BUN), creatinine, alanine aminotransferase (ALT), and aspartate aminotransferase (AST) were also measured using a SPOTCHEM™ automatic dry chemistry system (SP-4410; Arkray, Shanghai, Japan). The data are shown in FIG. 9.

Figure 9:
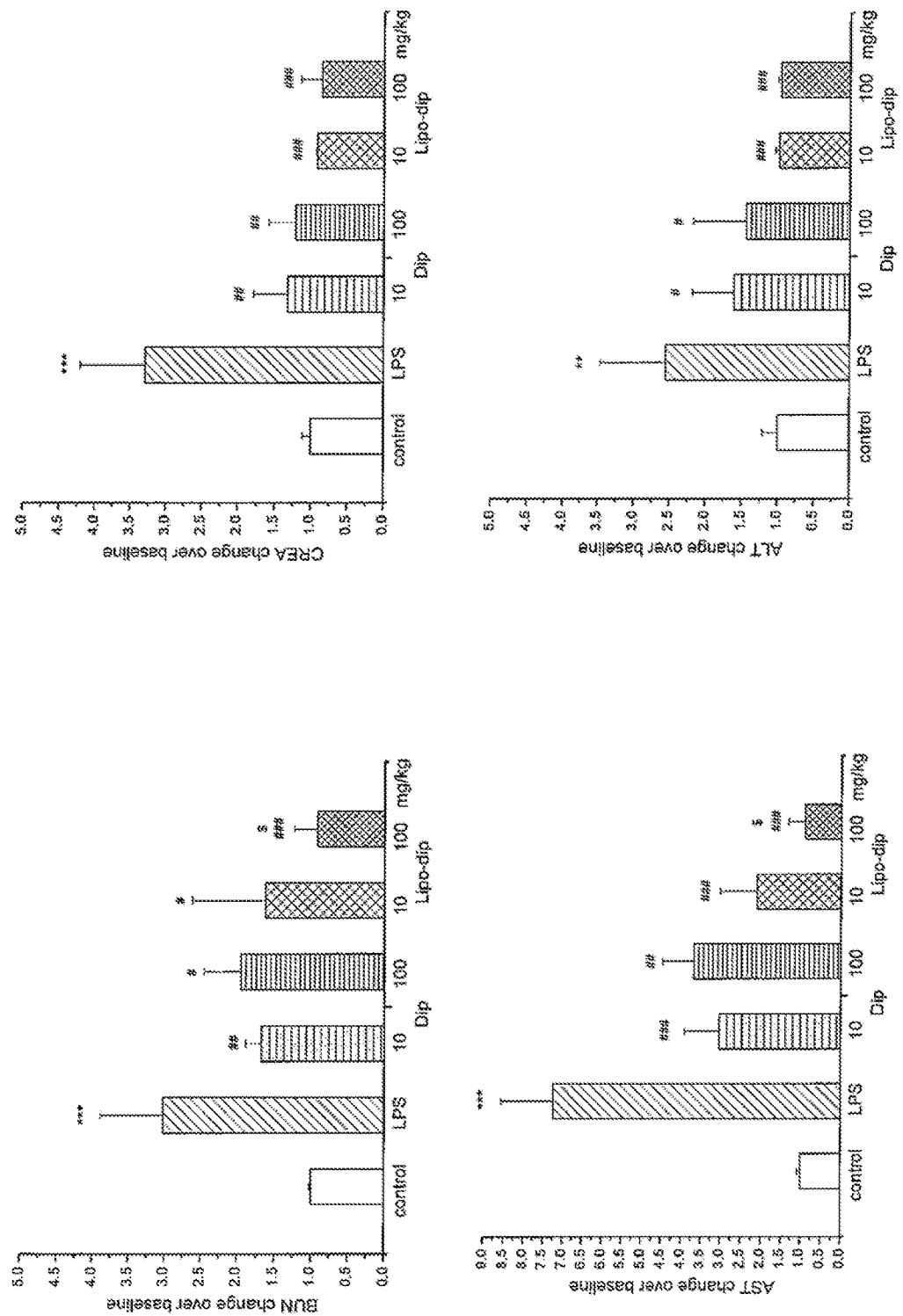
FIG. 9 shows the liver markers (AST, ALT) and kidney markers (BUN, Creatinine) after treatment.

FIG. 9 shows that LPS treatment induces liver and kidney injuries which significantly increase aspartate aminotransferase (AST), alanine aminotransferase (ALT), creatinine, and BUN levels in the blood. Treatments with low doses of dipyridamole or liposome dipyridamole attenuate LPS-induced increases of AST, ALT, creatinine, and BUN levels in serum. This indicates that dipyridamole has the therapeutic efficacy of treating acute or chronic liver and kidney inflammation as well as sepsis. In addition, since high dose of dipyridamole leads to changes in blood pressure and influences physiological conditions and survival rate, the dose-dependent efficacy of liposome dipyridamole may imply a broader range of applicable doses.

Example 5: Measurement of Tissue Injuries 5.1: IHC

Figure 10:
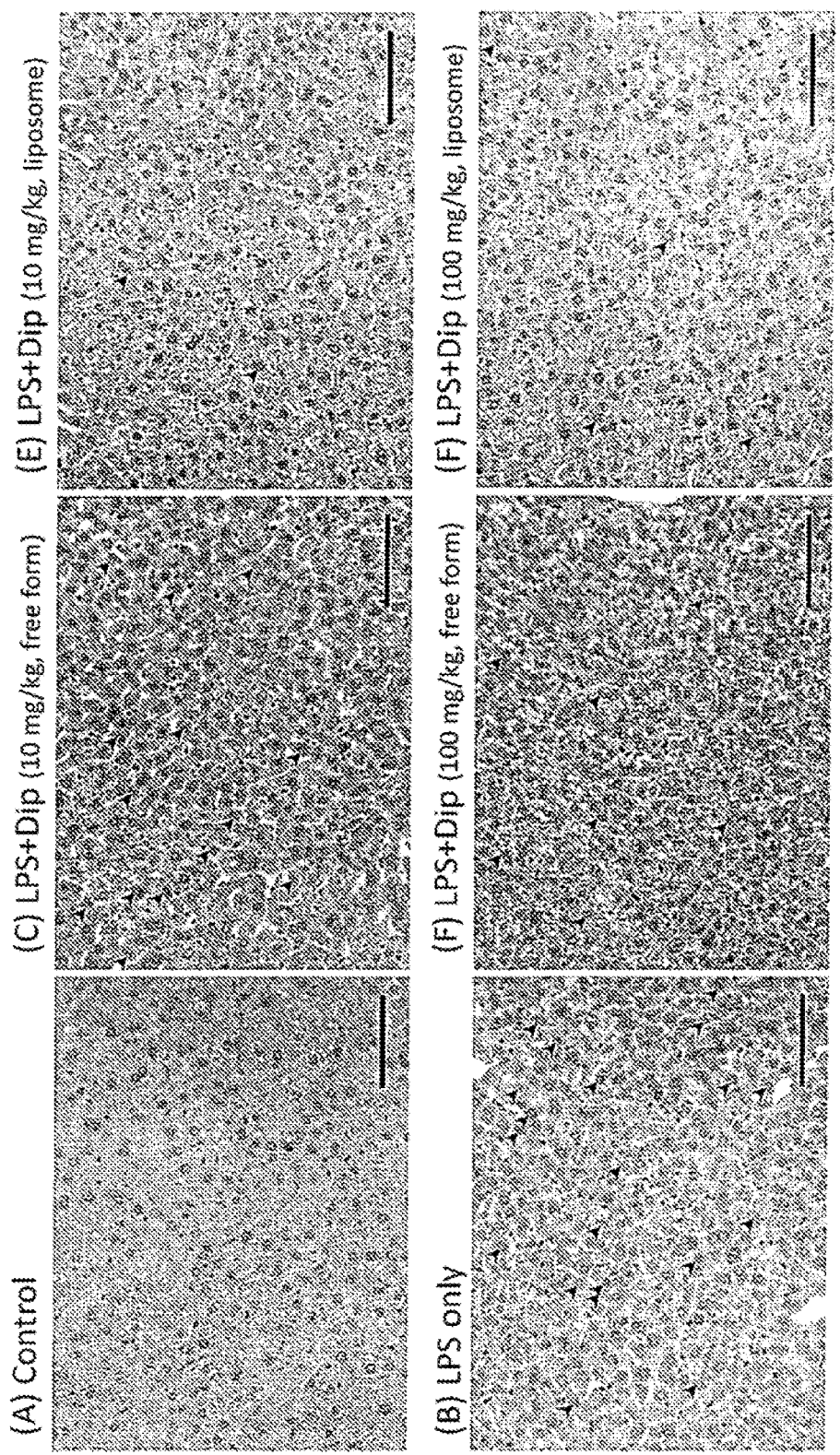
FIG. 10 shows the HE stain of liver tissues after treatment.
Figure 11:
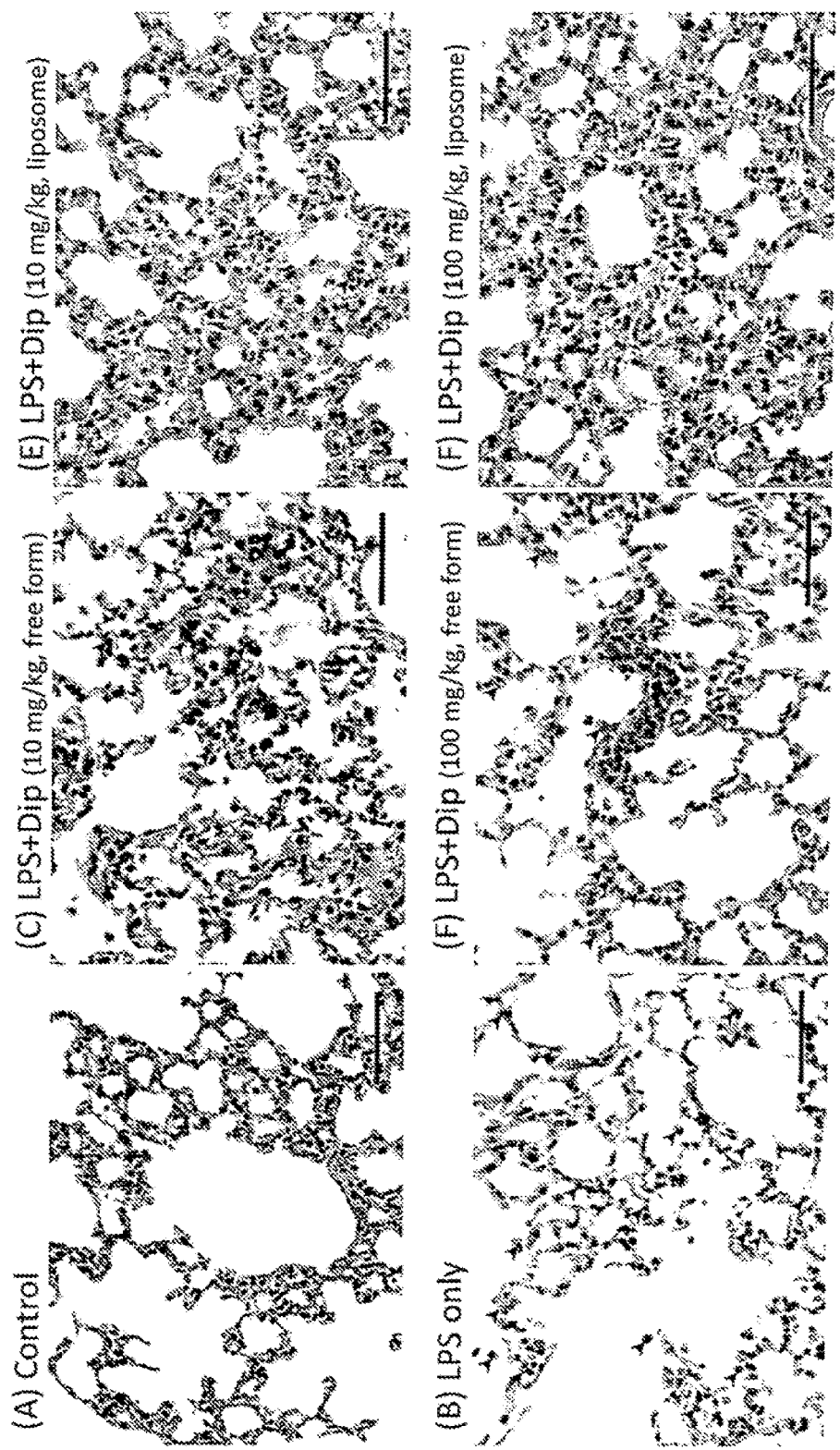
FIG. 11 shows the HE stain of lung tissues after treatment.

Paraffin-embedded sections (3 μm) were prepared from livers and lungs that were fixed in 10% phosphate-buffered formalin. Periodic acid-Schiff (PAS) stain was used for the analysis of morphology with light microscopy (Nikon E800; Melville, NY) by a blinded observer. For each mouse, at least 10 high-power fields were examined. The HE stain of liver and lung tissues are shown in FIGS. 10 and 11, respectively.

Excessive inflammation and tissue damage induced by accumulated macrophages and neutrophils were observed in HE-stained liver and lung sections 72 hours after LPS treatment. Post-treatment with dipyridamole or liposome dipyridamole attenuated tissue damage and inflammation. Compared to free form dipyridamole, liposome dipyridamole demonstrates better therapeutic efficacy in histology.

5.2: Activation State of PPARγ in Kidney and Liver

Mouse tissues were homogenized in 10 mM Tris-HCl (pH 7.5), 1 mM EDTA, 250 mM sucrose, 10 mM 2-mercaptoethanol (Nacarai tesque, Inc.), protease inhibitor (cOmplete, Mini, Roche Diagnostics) and phosphatase inhibitor (PhosSTOP, Roche Diagnostics). Six up-and-down strokes were used in a Braun Potter S homogenizer running at 1000 rpm. The homogenate was centrifuged (800 g), and the pellet was discarded. The supernatant was centrifuged again at 12,000 g for 10 min, and the resulting supernatant was collected. After the samples were collected, protein concentration was measured by Bradford assay. 6× sample buffer (0.8 mM Tris-HCl, 10 mM EDTA, 10% SDS, 60% glycerol, 0.6 M β-mercaptoethano, 0.06% bromophenol blue, pH 6.8) was added into 50 μg of whole cell proteins and an equal volume of lysis buffer was added into the samples. After being heated at 95° C. for 10 minutes to denature the proteins, the samples were immediately cooled on ice.

Figure 12A:
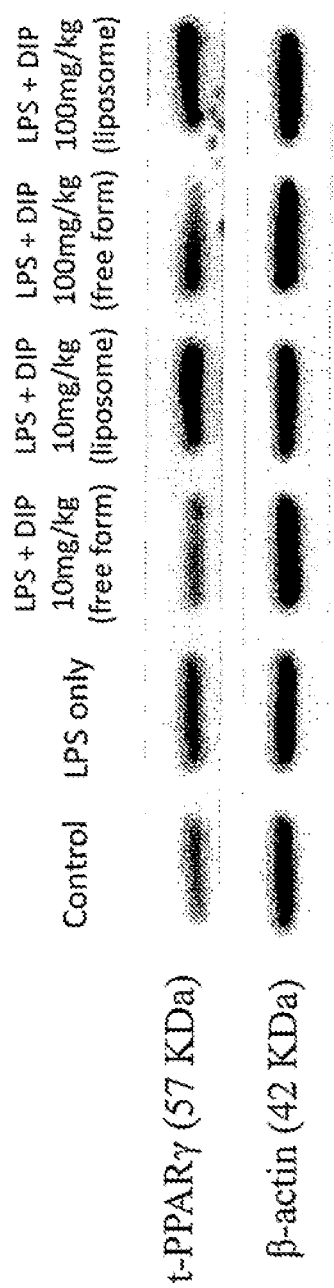
FIGS. 12a and 12b show the Western blot analysis of PPARγ expression in kidney and liver, respectively, after treatment.
Figure 12A:
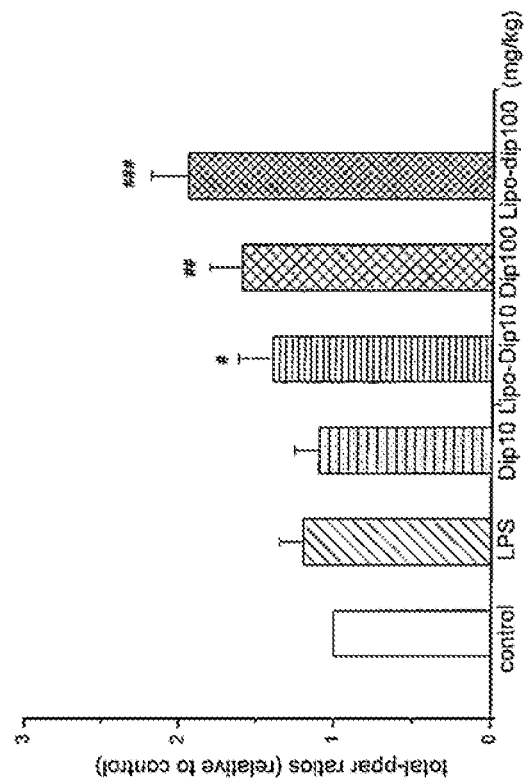
Figure 12B:
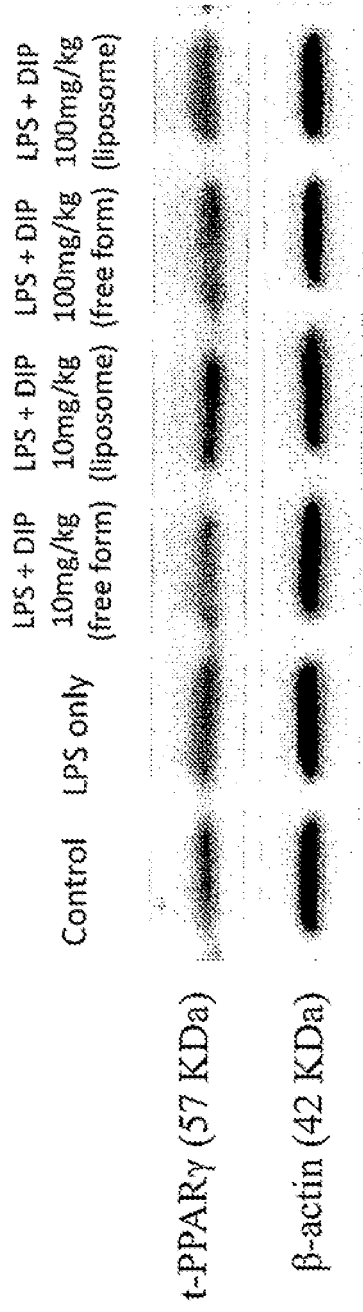
Figure 12B:
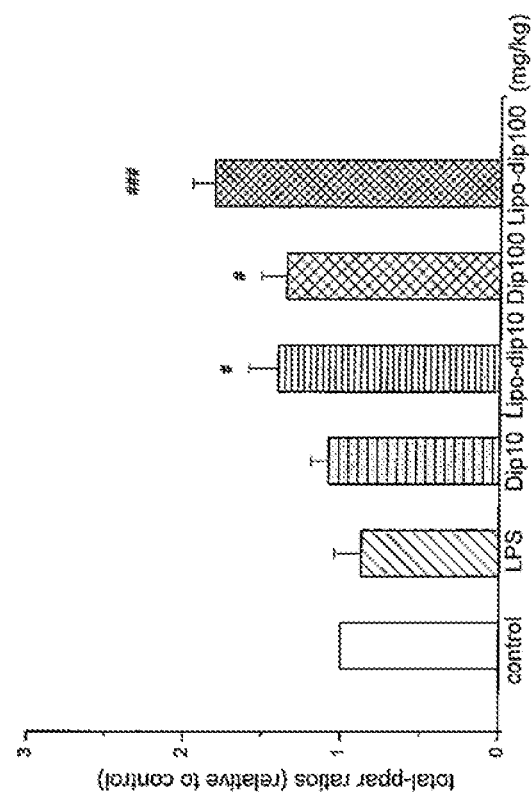

The samples were then separated by 10% SDS-PAGE electrophoresis (100 V) and transferred from the SDS-PAGE gels to PVDF membranes by wet blotting. The PVDF membranes were then treated with 5% skimmed milk at room temperature for 60 minutes to block non-specific binding. The membranes were incubated with primary antibody overnight at 4° C. and washed three times with PBST. The membranes were incubated with secondary antibody (anti-rabbit IgG, sigma) at room temperature for 60 minutes and washed three times with PBST. The membranes were then washed one more time with PBS and incubated with an enhanced chemiluminescence (ECL) substrate for detection. Photos of the images were taken using automated chemiluminescence and fluorescence imaging system (UVP Biospectrum). Antibody used: t-PPARγ (1:1000; abcam ab191407) and β-actin (1:1000; GeneTex GTX109639). The data of t-PPARγ expression in kidney and liver are shown in FIGS. 12a and 12b, respectively.

From the experimental results, it is clearly learned that no matter in kidney or liver tissue, dipyridamole or liposome dipyridamole has the activity to induce PPARγ expression in a dose dependent manner. Due to enhanced drug penetration into the cells by liposome through phagocytosis and fusion, the expression of PPARγ is greatly increased.

Example 6: The Effect of the Dipyridamole Liposome on Blood Pressure

Dipyridamole has a blood pressure-lowering effect. In the treatment of various acute and critical conditions, lowering the blood pressure may influence the prognosis of disease. Hence, detecting the effect of the dipyridamole liposome of the invention on blood pressure can permit evaluation of maximum dose feasible for clinical use.

Figure 13A:
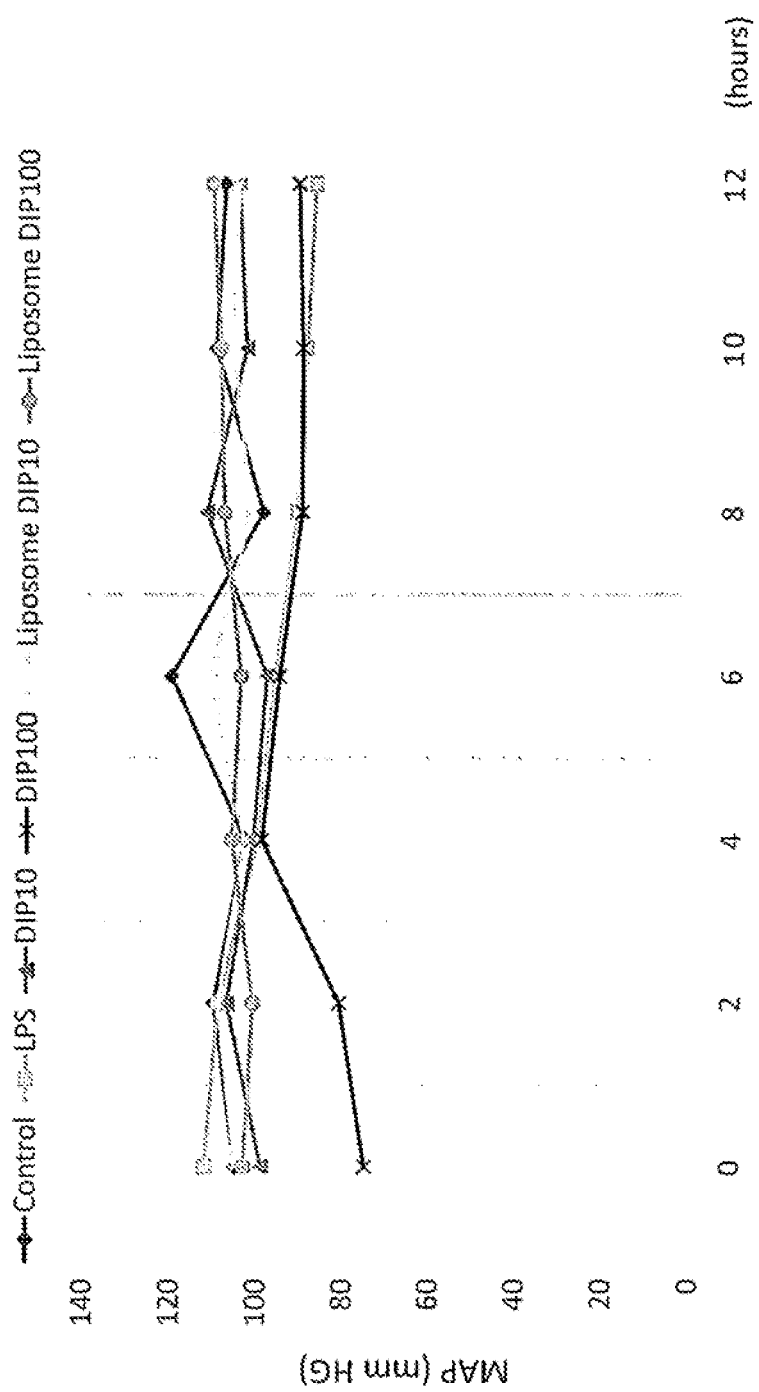
FIGS. 13a and 13b show the effect of dipyridamole and dipyridamole liposome on blood pressure.

Blood pressure of the mice was measured using a non-invasive blood pressure device after intravenous administration of the following agents: (1) saline, (2) LPS, (3) LPS prior to dipyridamole (free form), 10 mg/kg, (4) LPS prior to dipyridamole (free form), 100 mg/kg, (5) LPS prior to dipyridamole liposome, 10 mg/kg, and (6) LPS prior to dipyridamole liposome, 100 mg/kg. The results are shown in FIG. 13a.

Figure 13B:
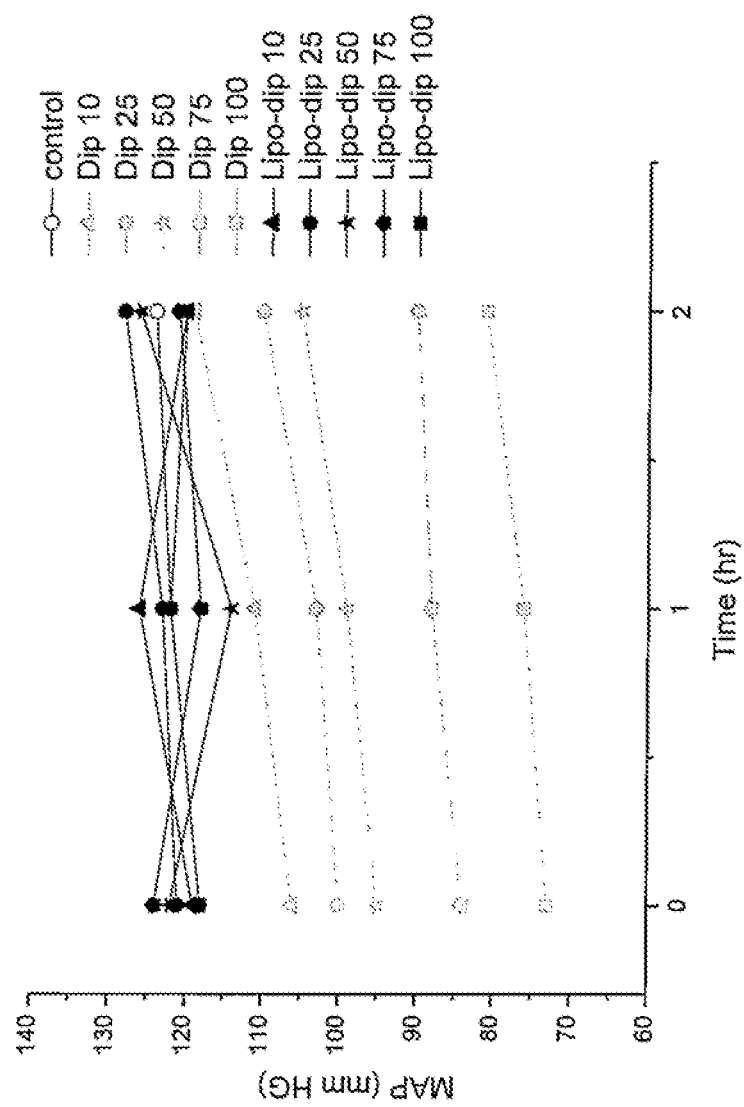

Additional test results with different doses (no LPS prior to drug treatment) are shown in FIG. 13b.

The above experimental data demonstrate that by increasing the ability of dipyridamole to enter the cell, the pharmacological mechanism of dipyridamole will be changed, leading to the increased activity of dipyridamole on PPARγ expression and the reduction of activity of dipyridamole on cell membrane, thereby reducing the stimulation of drug on blood vessel and the consequent severe interference on blood flow. By increasing the activity of dipyridamole on PPARγ expression, dipyridamole demonstrates potential in the treatment of multiple diseases. By the action of multiple mechanisms, the anti-inflammatory and anti-apoptosis activities of dipyridamole are increased via PPARγ pathway. Dipyridamole may be used for treating acute and severe diseases and small mammals without interfering with blood pressure.

What is claimed is:

1. A method of treating a PPARγ-related disorder or condition, comprising administering to a subject in need thereof a therapeutically effective amount of a compound of formula (I):

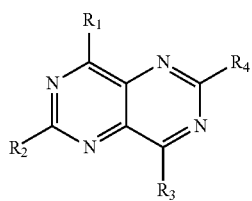

wherein $R_1$ and $R_3$ are piperidyl; and $R_2$ and $R_4$ are N,N-di(hydroxyethyl)amino,
or a pharmaceutically acceptable salt thereof,
wherein the PPARγ-related disorder or condition is acute kidney inflammation, acute kidney injury, kidney and lung injury, liver and kidney injury, liver and lung injury, or lung and liver and kidney multi-organ injury.

2. The method of claim 1, wherein the compound is encapsulated in a cell-penetrating drug delivery system.

3. The method of claim 2, wherein the cell-penetrating drug delivery system is a niosome, a polymersome, a nanoparticle, a liposome, a nano suspended particle, a solid lipid nanoparticle, a magnetic nano-carrier, a micelle, a macromolecular conjugate or a particulate drug carrier.

4. The method of claim 3, wherein the cell-penetrating drug delivery system is a liposome.

5. The method of claim 4, wherein the liposome has a diameter in the range of about 100-300 nm.

6. The method of claim 1, wherein the subject is a human or non-human mammal.

7. The method of claim 6, wherein the non-human mammal is a cat or a dog.

8. A method of treating a PPARγ-related disease or condition so as to reduce the side effect of vasodilation caused by drug and cell membrane receptor interaction, comprising administering to a subject in need thereof a pharmaceutical composition comprising a therapeutically effective amount of a compound of formula (I) or a pharmaceutically acceptable salt thereof as defined in claim 1 based on a cell-penetrating drug delivery system,
wherein the PPARγ-related disorder or condition is acute kidney inflammation, acute kidney injury, kidney and lung injury, liver and kidney injury, liver and lung injury, or lung and liver and kidney multi-organ injury.

9. The method of claim 8, wherein the cell-penetrating drug delivery system is a niosome, a polymersome, a nanoparticle, a liposome, a nano suspended particle, a solid lipid nanoparticle, a magnetic nano-carrier, a micelle, a cell-penetrating peptide, RGD peptides, a biodegradable nanoparticle, viral vectors, a macromolecular conjugate or a particulate drug carrier.

10. The method of claim 9, wherein the cell-penetrating drug delivery system is a liposome.

11. The method of claim 10, wherein the liposome has a diameter in the range of about 100-300 nm.

12. The method of claim 10, wherein the liposome is positively charged or bears a neutral charge.

13. The method of claim 8, wherein the therapeutically effective amount of a compound of formula (I) or a pharmaceutically acceptable salt thereof is in the range of 0.4-160 mg/kg.

14. The method of claim 8, wherein the subject is a human or non-human mammal.

15. The method of claim 14, wherein the non-human mammal is a cat or a dog.

* * * * *